(12) United States Patent
Koltz et al.

(10) Patent No.: US 12,011,148 B2
(45) Date of Patent: *Jun. 18, 2024

(54) SURGICAL SYSTEM INCLUDING POWERED ROTARY-TYPE HANDPIECE

(71) Applicant: MEDTRONIC XOMED, INC, Jacksonville, FL (US)

(72) Inventors: Michael L. Koltz, Jacksonville, FL (US); Christopher L Fair, Jacksonville, FL (US); Michael S. Ferrell, Jacksonville, FL (US); Andrzej Klimaszewski, Jacksonville, FL (US); David J. Little, II, Jacksonville, FL (US); Manfred K. Luedi, Jacksonville, FL (US); Gerould Norman, Jacksonville, FL (US); Robert K. Vaccaro, Jacksonville, FL (US)

(73) Assignee: MEDTRONIC XOMED, INC, Jacksonville, FL (US)

( * ) Notice: Subject to any disclaimer, the term of this patent is extended or adjusted under 35 U.S.C. 154(b) by 105 days.

This patent is subject to a terminal disclaimer.

(21) Appl. No.: 17/590,842

(22) Filed: Feb. 2, 2022

(65) Prior Publication Data

US 2022/0151597 A1    May 19, 2022

Related U.S. Application Data

(63) Continuation of application No. 16/573,505, filed on Sep. 17, 2019, now Pat. No. 11,272,909, which is a
(Continued)

(51) Int. Cl.
*A61B 17/00* (2006.01)
*A61B 17/16* (2006.01)
*A61B 17/70* (2006.01)

(52) U.S. Cl.
CPC .......... *A61B 17/00* (2013.01); *A61B 17/1622* (2013.01); *A61B 17/1626* (2013.01); *A61B 17/7074* (2013.01); *A61B 17/162* (2013.01)

(58) Field of Classification Search
CPC .... H01H 9/061; H01H 9/063; A61B 19/5244; A61B 2019/464; A61B 2019/502; A61B 17/1626
(Continued)

(56) References Cited

U.S. PATENT DOCUMENTS

| 4,473,226 A | 9/1984 | Siegel et al. |
| 4,741,731 A | 5/1988 | Starck et al. |

(Continued)

FOREIGN PATENT DOCUMENTS

| AU | 2013232167 | 6/2017 |
| CA | 2867140 | 2/2021 |

(Continued)

OTHER PUBLICATIONS

Translation of JP Office Action, dated Aug. 28, 2016, 4 pages.
KR Office Action, PCT/US2013/030949, dated Sep. 22, 2020, 5 pages.

*Primary Examiner* — Eduardo C Robert
*Assistant Examiner* — Tara Rose E Carter
(74) *Attorney, Agent, or Firm* — Carter, DeLuca & Farrell LLP

(57) ABSTRACT

A surgical system which may include a controller, a data entry device, a powered surgical handpiece and a surgical tool adapted to couple to the surgical handpiece. The surgical handpiece can include motor direction control and feedback, safety stop features, stimulation and nerve integrity monitoring, a tool connector assembly configured to retain a variety of surgical tools and optional navigation and/or electric ratcheting features.

10 Claims, 20 Drawing Sheets

Related U.S. Application Data continuation of application No. 13/799,598, filed on Mar. 13, 2013, now Pat. No. 10,456,122.

(60) Provisional application No. 61/610,204, filed on Mar. 13, 2012.

(58) Field of Classification Search
USPC ............ 606/86 R, 80, 81, 160–183; 388/937
See application file for complete search history.

(56) References Cited

U.S. PATENT DOCUMENTS

| | | | |
|---|---|---|---|
| 5,207,697 A | 5/1993 | Carusillo et al. | |
| 5,910,152 A | 6/1999 | Bays | |
| 6,050,989 A | 4/2000 | Fox et al. | |
| 6,126,670 A | 10/2000 | Walker et al. | |
| 6,500,169 B1 | 12/2002 | Deng | |
| 6,635,067 B2 | 10/2003 | Norman | |
| 8,454,640 B2 | 6/2013 | Johnston et al. | |
| 10,456,122 B2 | 10/2019 | Koltz et al. | |
| 11,272,909 B2* | 3/2022 | Koltz ................. | A61B 17/7074 |
| 2002/0020538 A1* | 2/2002 | Giardino ............ | B25B 23/1405 |
| | | | 173/180 |
| 2003/0181934 A1 | 9/2003 | Johnston et al. | |
| 2005/0283148 A1 | 12/2005 | Janssen et al. | |
| 2006/0206100 A1 | 9/2006 | Eskridge et al. | |
| 2007/0021766 A1 | 1/2007 | Belagali et al. | |
| 2009/0210041 A1 | 8/2009 | Kim et al. | |
| 2009/0261536 A1 | 10/2009 | Beale et al. | |
| 2009/0264887 A1 | 10/2009 | Beale et al. | |
| 2009/0264893 A1 | 10/2009 | Beale et al. | |
| 2009/0264940 A1* | 10/2009 | Beale ..................... | A61B 90/39 |
| | | | 606/86 R |
| 2009/0299439 A1 | 12/2009 | Mire et al. | |
| 2011/0009699 A1 | 1/2011 | Slenker et al. | |
| 2011/0202023 A1 | 8/2011 | Stanton et al. | |
| 2011/0248653 A1* | 10/2011 | Brotto ................. | H01R 13/112 |
| | | | 318/139 |
| 2011/0270120 A1 | 11/2011 | McFarlin et al. | |
| 2012/0274253 A1 | 11/2012 | Fair et al. | |
| 2020/0008787 A1 | 1/2020 | Koltz et al. | |

FOREIGN PATENT DOCUMENTS

| | | |
|---|---|---|
| CN | 1301087 C | 2/2007 |
| EP | 1803406 B1 | 3/2011 |
| EP | 2825105 | 1/2015 |
| JP | 2001314411 | 11/2001 |
| JP | 2005520618 | 7/2005 |
| KR | 20090097249 A | 9/2009 |
| KR | 20110010828 A | 2/2011 |
| WO | 2007002230 | 1/2007 |
| WO | 2013138481 | 9/2013 |

* cited by examiner

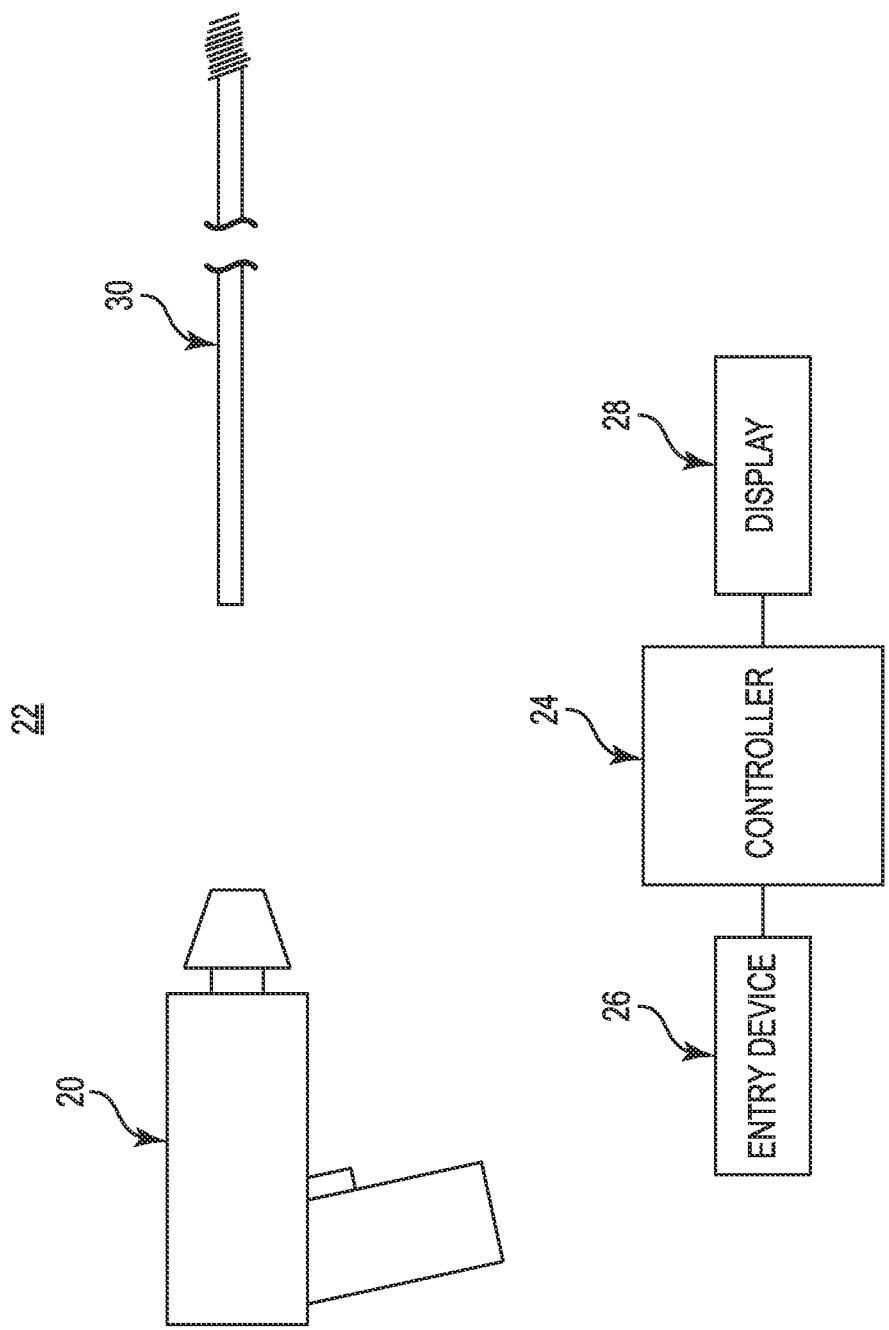

SURGICAL SYSTEM INCLUDING POWERED ROTARY-TYPE HANDPIECE

CROSS-REFERENCE TO RELATED APPLICATIONS

This application is a Continuation of application Ser. No. 16/573,505 entitled "SURGICAL SYSTEM INCLUDING POWERED ROTARY-TYPE HANDPIECE", filed Sep. 17, 2019, which is a Continuation of application Ser. No. 13/799,598 entitled "SURGICAL SYSTEM INCLUDING POWERED ROTARY-TYPE HANDPIECE", filed Mar. 13, 2013, now U.S. Pat. No. 10,456,122, which claims the benefit of U.S. Provisional Application No. 61/610,204, entitled "SURGICAL SYSTEM INCLUDING POWERED ROTARY-TYPE HANDPIECE", filed Mar. 13, 2012, both of which are incorporated by reference herein.

BACKGROUND

The present disclosure generally relates to powered handpieces for driving surgical instruments or tools. More particularly, it relates to powered rotary-type surgical handpieces and corresponding control systems for interfacing with and controlling operation thereof.

Powered surgical handpieces are commonly used in many medical specialties to drive surgical tools. For example, powered surgical handpieces are used to drive surgical drills, blades or cutting instruments in performing various diverse cutting-type functions including drilling, tapping, resection, dissection, debridement, shaving, pulverizing, and shaping of anatomical tissue. In the areas of ENT/head/neck and spine surgery, the handpieces are typically configured for selective coupling to, and driving of, a variety of different rotary-type surgical instruments that are each designed to perform a specific procedure. During use, based upon the specific surgical procedure, the surgeon selects the appropriate surgical tool and mounts it to the powered handpiece. The powered handpiece is then operated to move one or more components of the tool (e.g., rotation, oscillation) required to perform the surgical procedure. Additional procedural steps can later be performed by mounting a differently-styled tool to the same powered handpiece. As a point of reference, the rotational speeds typically required by a powered surgical handpiece for spinal or other hard bone surgical procedures is in the range of about 10-250 rpm. ENT/head/neck procedures range from about 500 rpm for a laryngeal skimming operations to in excess of 60,000 rpm for high-speed drill operations.

In addition to motor improvements, such as use of brushless DC motors, overall systems have been developed for use with the powered rotary-type surgical handpiece and related surgical tools. A typical system, in addition to a powered handpiece and one or more rotary-type surgical tools or instruments, includes a control console and a cable that connects the handpiece to the console. The control console is configured to activate and/or control energization of the motor otherwise associated with the powered surgical handpiece. For example, a hand or foot switch can be provided as part of the system. Depending upon the surgeon's manipulation of the foot or hand switch, a corresponding signal is delivered to the control console that, in turn, energizes the handpiece to a corresponding speed.

The improved capabilities of powered surgical handpieces, as well as the vast number of surgical tools now available, have undoubtedly greatly increased the number of spine and ENT/head/neck procedures that a surgeon can perform utilizing a single surgical system. With these improvements, however, surgeons now desire even greater performance, operational capabilities, and safety with a single powered handpiece. For example, surgeons desire the ability to rotate a selected surgical tool under low speed/high torque conditions, using only surgeon's finger to control the rotational speed and direction. Nerve integrity monitoring via the same powered handpiece otherwise operating the surgical instrument, safety over-rides, constant operational feedback, etc., are also features of keen interest to many surgeons. While conventional engineering is likely capable of adding one of these features to an existing powered handpiece and/or corresponding control console, known powered handpiece configurations cannot accommodate all desired features. As a point of reference, the powered surgical handpiece must not only provide necessary control over operation of the surgical instrument, but must be ergonomically sized and shaped to be comfortably held and manipulated by the surgeon for an extended length of time.

In light of the above, a need exists for a rotary-type powered surgical handpiece providing enhanced performance capabilities in an ergonomically-sized housing, as well as control console-enabled feedback and control.

SUMMARY

In an embodiment, a surgical handpiece comprises a housing forming a grip, a drive shaft rotatably maintained by the housing, a trigger assembly adapted to generate a signal indicative of a speed desired by user, the trigger assembly includes a trigger maintained by the grip; a mode selection assembly adapted to generate a signal indicative of a direction of rotation desired by a user, the mode selection assembly includes a collar maintained by the housing adjacent the grip and the handpiece is configured such that when the grip is grasped in a palm of a user's hand, an index finger of the user's palm can selectively interact with the trigger and the collar. The collar can be rotatable about an axis of the drive shaft.

In another embodiment, a surgical system includes a surgical handpiece having a motor, a controller connected to the surgical handpiece and programmed to interface with the surgical handpiece, the controller can include a data entry device and a display screen, where the controller can be programmed to display a torque applied by the surgical handpiece on the display screen and the displayed torque is based on a motor current feedback.

In another embodiment a surgical system for use in spine surgery comprises a surgical handpiece, a controller connected to the surgical handpiece and programmed to interface with the surgical handpiece, where the controller is configured to detect a failure of a surgical tool associated with the handpiece or of a bone to which the surgical tool is being applied and in response, is programmed to stop the motor or control a current delivered to the motor if a failure is detected; a stimulator assembly adapted to provide an electrical current stimulation to the drive shaft to provide nerve integrity monitoring (NIM); a navigation adapter coupled to the surgical handpiece.

Surgical tools according to the disclosure may include a variety of working ends and may include an interface end (configured to interface with a portion of the surgical handpiece) having a bare tool shaft where the bare shaft includes no detents, grooves or indentations at the interface end or along the entire surgical tool. Surgical tools may also include flat surfaces and surgical tools useful with the present disclosure may include conventional interface ends.

Surgical handpieces of the present disclosure can include a tool connector assembly adapted for attachment to the surgical handpiece and configured to retain a variety of surgical tools. The tool connector assembly can include a locked state and an unlocked state where the assembly retains a surgical tool in the locked state. Tool connector assemblies may include one or more balls, the tool connector assembly configured to secure a tool shaft of a surgical tool upon initial engagement of the tool shaft with the balls.

Surgical handpieces of the present disclosure may include a motor assembly configured to rotate the drive shaft via a gear train, the gear train including a gear reduction system configured to increase an output torque of the motor while reducing an output speed of the drive shaft.

Surgical handpiece of the present disclosure may include a trigger assembly configured to sense a position of the trigger and generate a signal to a controller indicative of the sensed position and may further be configured to generate another signal to the controller indicative of a user's finger being in contact with or not in contact with the trigger. Signals generated by the trigger assembly may be inverted with respect to one another.

Portions of the surgical handpiece may optionally or advantageously liquidly sealed within the surgical handpiece.

Controllers used with surgical systems of the present disclosure can be configured to limit a torque rate of change over time applied by a surgical handpiece based upon a motor current feedback of the surgical handpiece motor. Controllers of the present disclosure may also monitor the torque rate of change over time and detect a failure of a surgical tool attached to the surgical handpiece or of a bone to which a surgical tool is applied, (i.e., is affecting or treating). A controller may be programmed to stop the motor or control a current delivered to the motor if a failure of the surgical tool or bone is detected.

Surgical systems or surgical handpieces of the present disclosure can include a stimulator assembly associated with the surgical handpiece and adapted to provide an electrical current stimulation path to a drive shaft of the surgical handpiece and thereby to a surgical tool associated with the surgical handpiece. The stimulation energy can provide nerve integrity monitoring. Drive shafts can include a first stationary state and a second rotating state where the surgical handpiece is configured to provide stimulation energy to the surgical tool when the drive shaft is in either state.

Surgical systems and handpieces of the present disclosure are optionally configured to interact with an image guidance system and thus surgical handpieces may thus be configured to receive an optional navigation adapter. Surgical handpieces of the present disclosure may also include electric ratchet features.

BRIEF DESCRIPTION OF THE DRAWINGS

FIG. 1 is a block diagram of a surgical system including a rotary-type powered surgical handpiece in accordance with principles of the present disclosure;

DETAILED DESCRIPTION

Figure 2A:
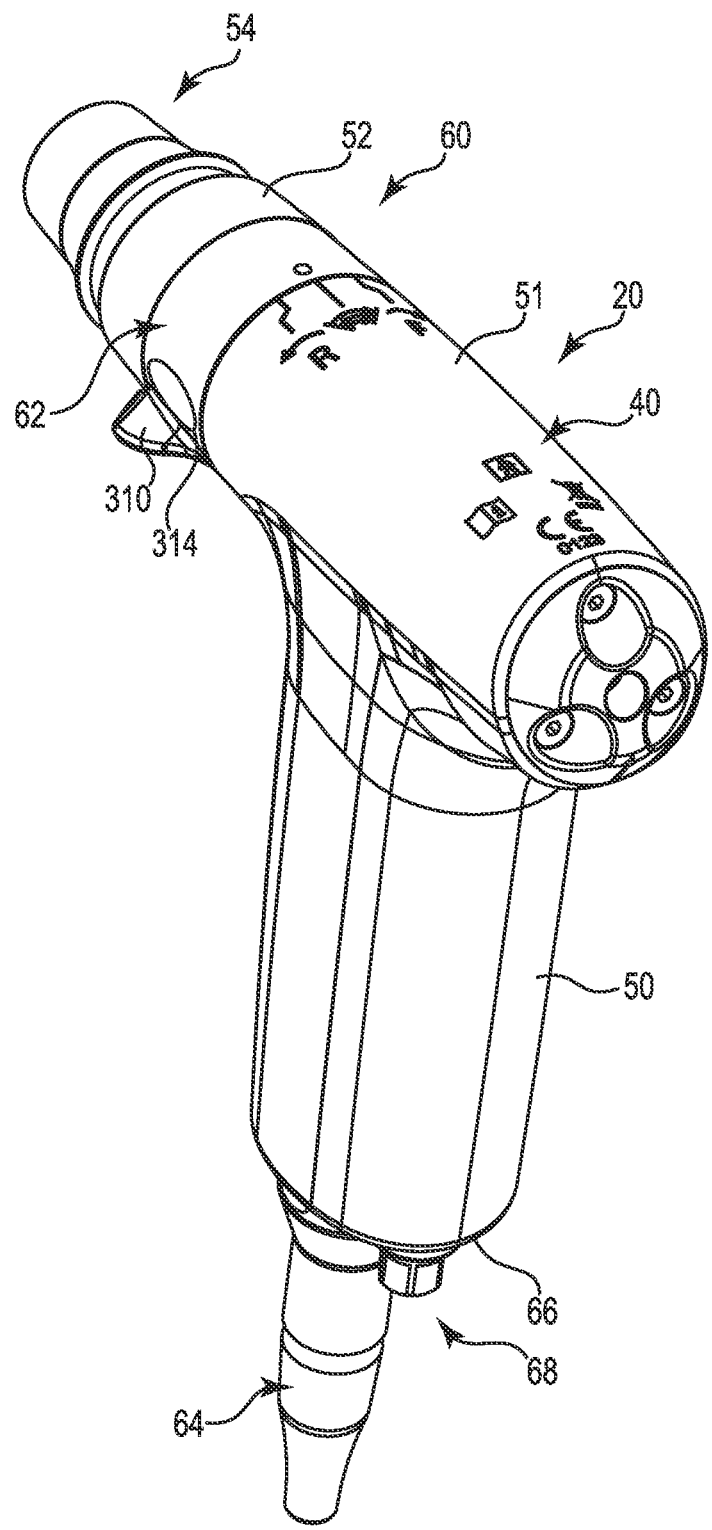
FIGS. 2A and 2B are perspective views of a rotary-type powered surgical handpiece in accordance with principles of the present disclosure.

One embodiment of a rotary-type powered surgical handpiece 20 in accordance with principles of the present disclosure is shown in FIG. 1. In some embodiments, the handpiece 20 is provided and/or is operated as part of a system 22 that further includes a controller 24. Where provided, the controller 24 has a microprocessor and can include (or be electronically connected to) one or more components such as a data entry device 26 and a display screen 28. Regardless, and in general terms, the handpiece 20 is configured to selectively receive a surgical instrument or tool 30 as described below. Once connected to the controller 24, the system 22, and in particular the handpiece 20, is operated by a user to rotationally drive the instrument 30 in performing a desired surgical procedure, with the controller 24 providing desired feedback and optional override control over the handpiece 20 based on information automatically signaled from the handpiece 20. Various features can be incorporated into the handpiece 20 and/or into the system 22 as a whole, including motor control and feedback, stimulation energy or nerve integrity monitoring, quick connect/disconnect between the handpiece 20 and the tool 30, safety over-rides based on user finger sensing, mode-function-direction control at the handpiece 20, high torque operation at very low and high speeds, etc., as described below.

Figure 2B:
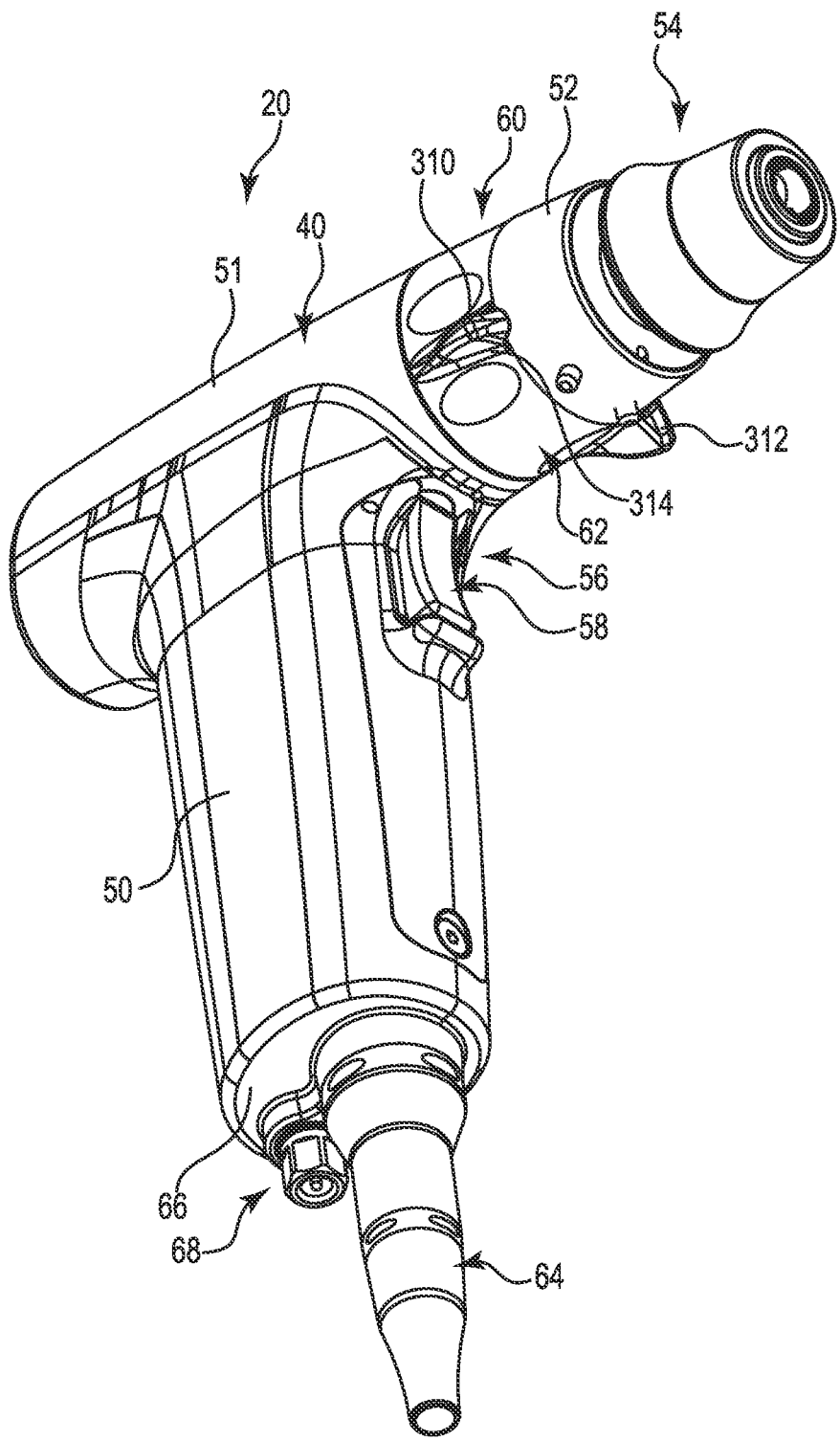

One embodiment of the powered handpiece 20 is shown in greater detail in FIGS. 2A and 2B. In general terms, the handpiece 20 includes a housing 40 that contains various internal components (e.g., a motor, gear train, etc.) described below, and forms a grip or handle 50, a head 51, and a nose 52. A tool connector assembly 54 is coupled to the nose 52 and is generally configured to facilitate selective coupling with the tool 30 (FIG. 1). A trigger assembly 56 (referenced generally) is coupled to the housing 40, and includes an actuator or trigger 58 disposed along the grip 50. Actuation or movement of the trigger 58 prompts the handpiece 20 to rotate an attached tool 30 at a speed corresponding with an extent of movement of the trigger 58. In this regard, the trigger 58 is arranged relative to the grip 50 such that when the grip 50 is held in a user's hand, a finger (e.g., index finder) of the user's hand can readily interface with the trigger 58. This arrangement, along with the head 51/nose 52 locating the tool 30 above and forward of the trigger 58, provides the powered handpiece 20 with a pistol grip-like shape. A mode selection assembly 60 (referenced generally) includes a first collar comprising an actuator or rotatable mode selection assembly collar 62 carried by the nose 52. Manual actuation or rotation of the collar 62 prompts the powered handpiece 20 to rotate the tool 30 in a selected direction or mode (e.g., forward, reverse, or oscillate). Electrical cabling 64 extends from a lower end 66 of the housing 40 and carries one or more wires or cables connected to various internal components of the powered handpiece 20. For example, the cabling 64 can carry a power supply cable or wires that delivers power to the handpiece motor (hidden), signal cables or wires connected to various sensors (not shown) provided with the trigger assembly 56 and/or the mode selection assembly 60, etc. Further, a stimulator assembly 68 (referenced generally) includes a component mounted to the lower end 66 and is generally configured for electrical connection to cabling (not shown) providing stimulation energy for use in a nerve integrity monitoring mode of operation.

Figure 3A:
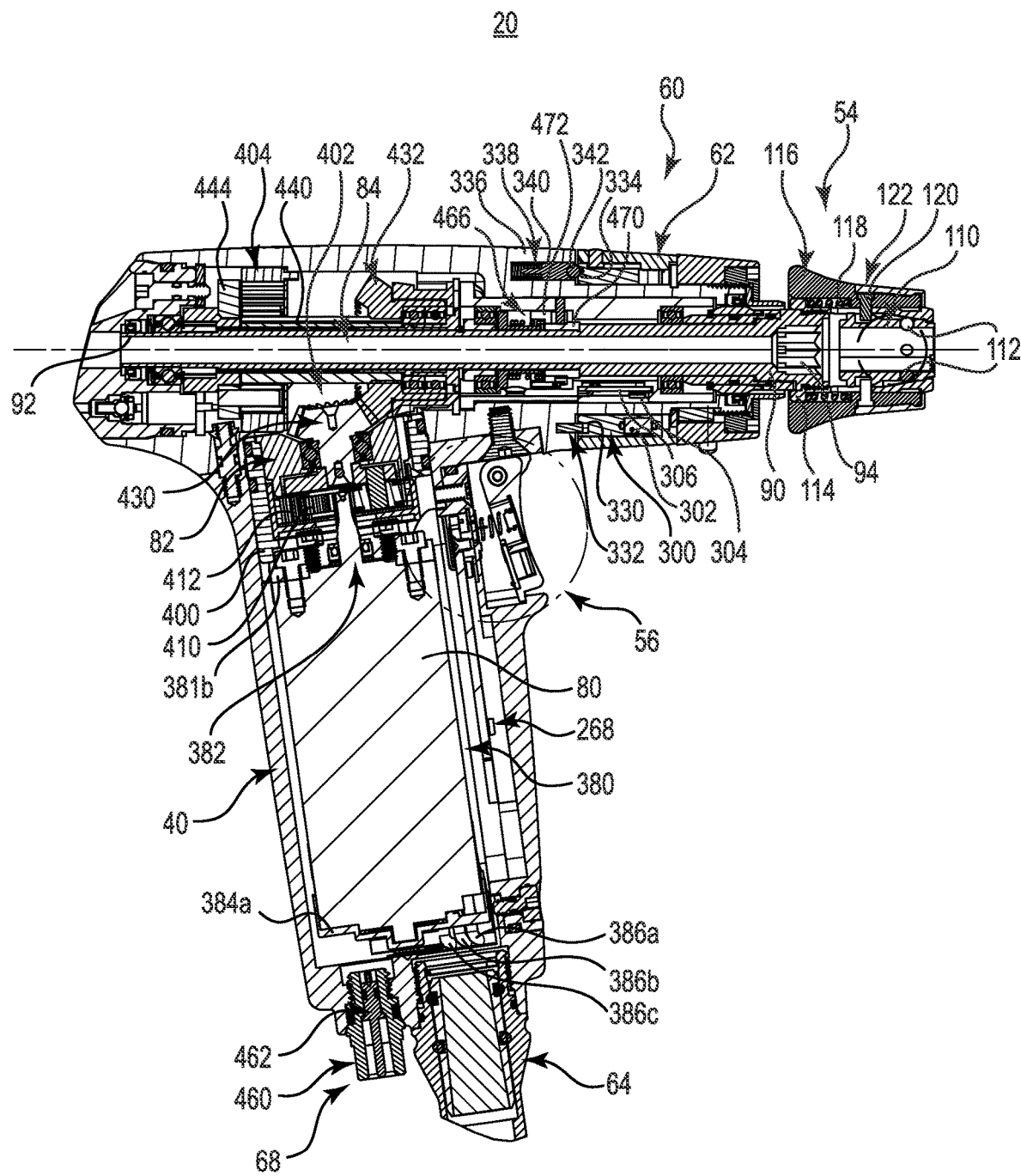
FIG. 3A is a transverse side cross-sectional view of the handpiece of FIG. 2A.
Figure 3B:
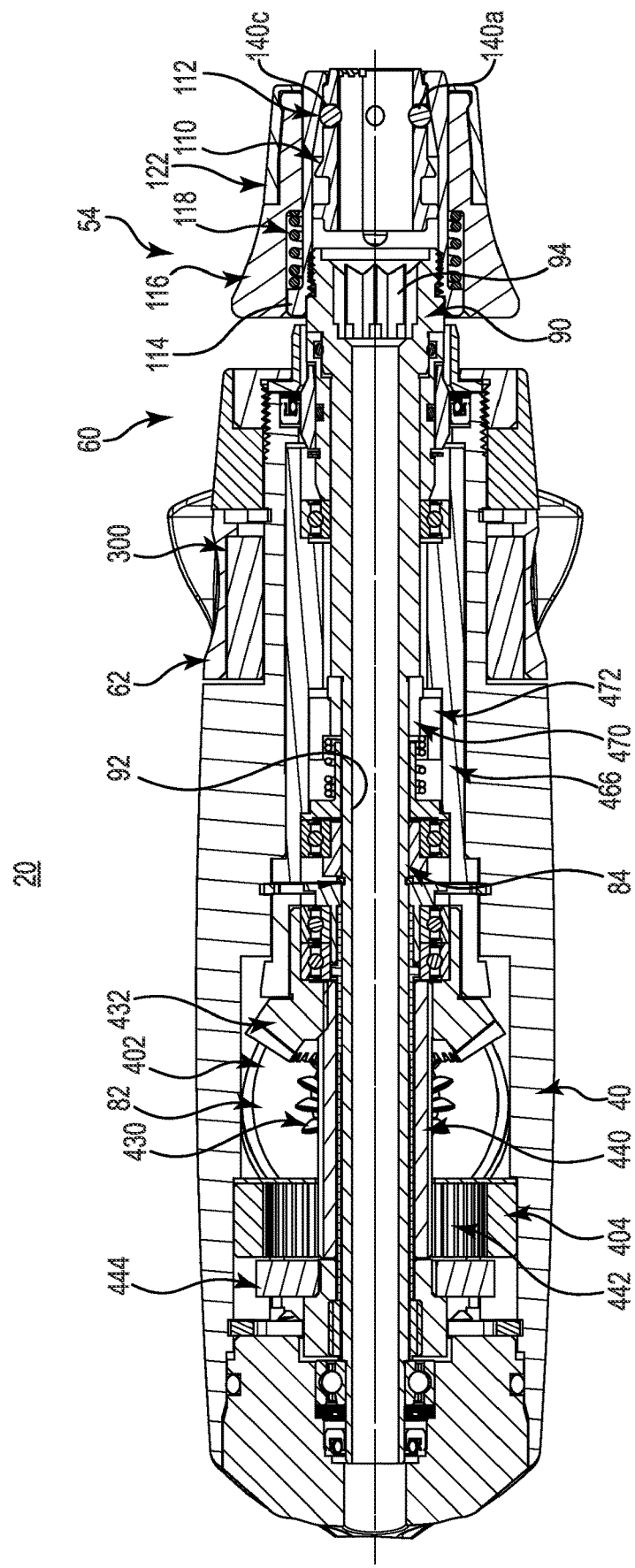
FIG. 3B is a longitudinal cross-sectional view of the handpiece of FIG. 2A taken along a plane passing through a main drive shaft component thereof.
Figure 3C:
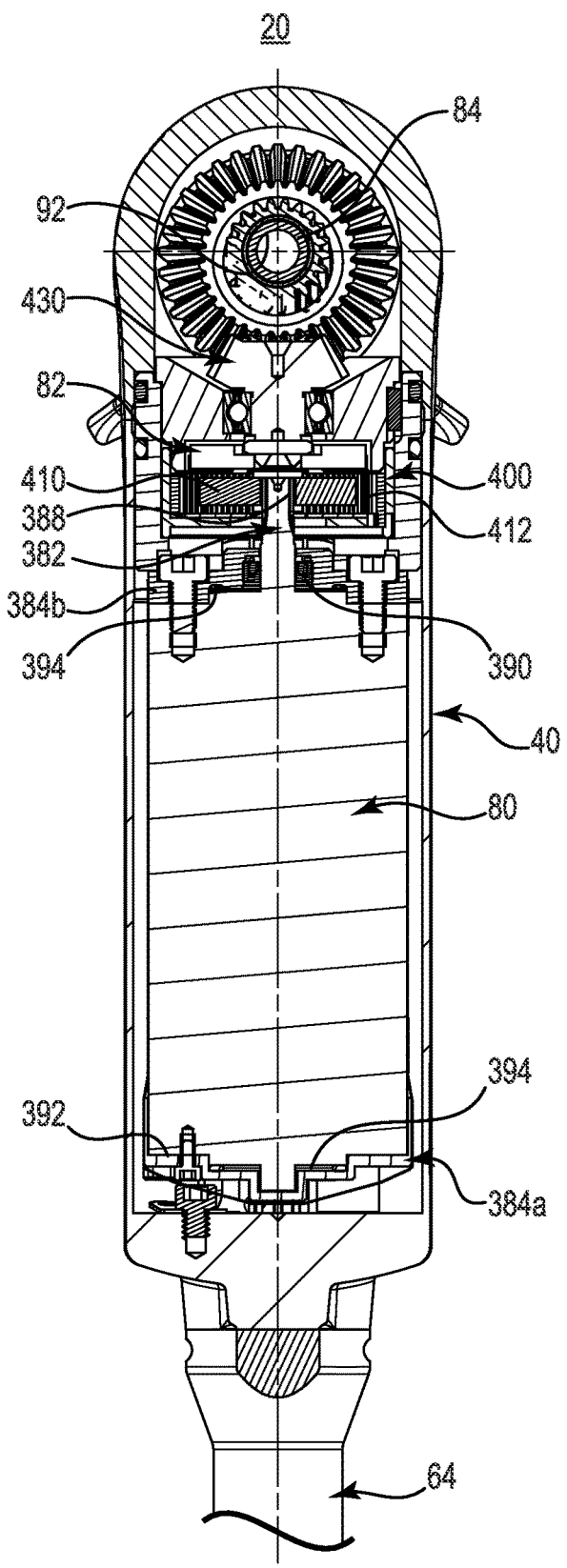
FIG. 3C is a lateral side cross-sectional view of the handpiece of FIG. 3A taken along a plane passing through a motor component thereof.

Internal components of the powered handpiece 20 are shown in greater detail in FIGS. 3A-3C, and generally include the tool connector assembly 54, the trigger assembly 56, the mode selection assembly 60, a motor 80, a gear train 82, and a main drive shaft 84. Each of the components is described in greater detail below. In general terms, the tool connector assembly 54 selectively mounts or connects a selected tool 30 (FIG. 1) with the drive shaft 84. The motor 80 operates to rotate the drive shaft 84 (and thus the tool 30 connected thereto) via the gear train 82 as prompted by user operation of the trigger assembly 56. In this regard, the mode selection assembly 60 is operable by a user to prompt a desired direction or mode of rotation. Finally, various electrical signals are carried to and from the powered handpiece 20 via the cabling 64. The handpiece 20 can further include one or more additional components or assemblies, for example components carried by the housing 40 and rotatably supporting the drive shaft 84.

As best shown in FIGS. 3A and 3B, the drive shaft 84 defines a distal region 90 and forms a central lumen 92. The lumen 92 can extend an entire length of the drive shaft 84 as shown, or alternatively can be formed at only the distal region 90. With embodiments in which the lumen 92 runs an entire length of the drive shaft 84, the handpiece 20 provides a cannulation feature in which a cannula, guide wire, etc., can be inserted through the drive shaft 84 (and the tool connector assembly 54). Regardless, the distal region 90 forms an interior engagement surface 94 configured for engaging an adaptor or interface end of a surgical tool (not shown). The engagement surface 94 can assume a variety of forms conventionally employed with powered surgical handpieces, such as a square drive as shown.

Tool Connector Assembly

The distal region 90 of the drive shaft 84 projects from the nose 52 and provides an exterior surface configured to receive the tool connector assembly 54. With this in mind, in some embodiments the tool connector assembly 54 includes a plunger 110, one or more balls 112, a second, or tool connector assembly collar 114, a sleeve 116, a spring 118, one or more pins 120, and a cover 122 as shown in greater detail in FIG. 3D. In general terms, the plunger 110 is configured to receive an interface end (not shown) of a rotary-type surgical tool (e.g., the tool 30 of FIG. 1). The balls 112 are carried by the plunger 110 and are selectively biased radially inwardly relative to the plunger 110 by the collar 114 for locking the tool interface end relative to the plunger 110. The sleeve 116 is slidably disposed over the collar 114 to selectively force a region of the collar 114 (otherwise aligned with the balls 112) radially inward. The spring 118 biases the sleeve 116 to the forward or locked arrangement (relative to the collar 114) shown in the figures, with the pins 120 capturing the collar 114 and the sleeve 116 to one another. Finally, the cover 122 captures the pins 120 relative to the collar 114.

Figure 4A:
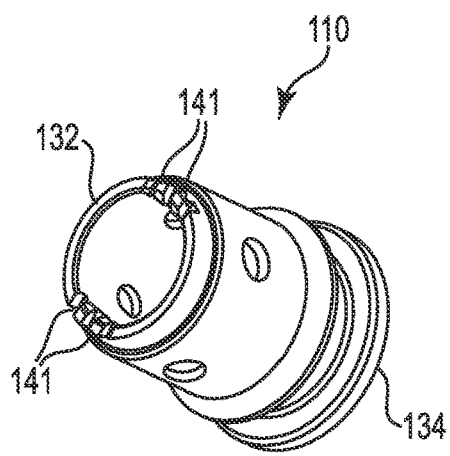
FIG. 4A is a front perspective view of a plunger component of the tool connector assembly of FIG. 3D.
Figure 4B:
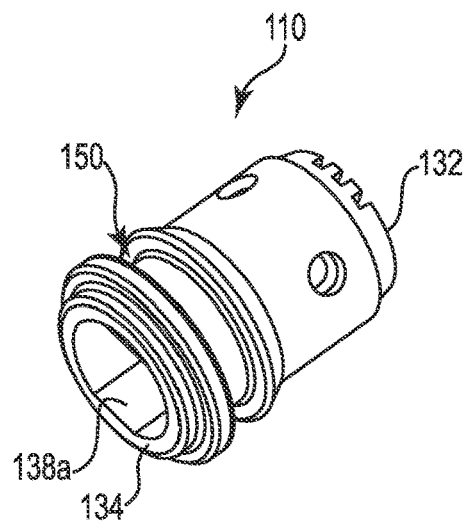
FIG. 4B is a rear perspective view of the plunger of FIG. 4A.
Figure 4C:
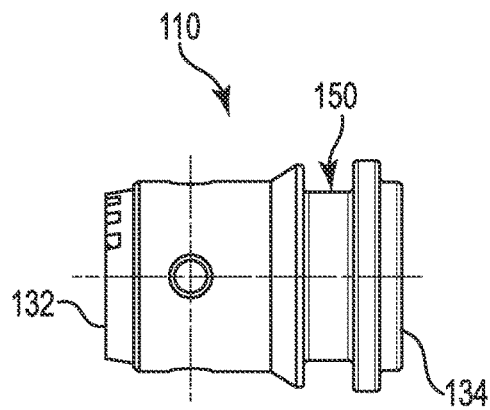
FIG. 4C is a side view of the plunger of FIG. 4A.
Figure 4D:
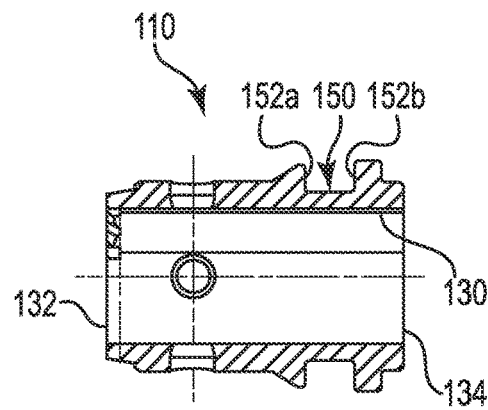
FIG. 4D is a longitudinal cross-sectional view of the plunger of FIG. 4A.

One embodiment of the plunger 110 is shown in greater detail in FIGS. 4A-4F. The plunger 110 is a generally cylindrical body formed of a hardened material (e.g., stainless steel), and defines a central bore 130 extending between, and open at, leading and trailing ends 132, 134. The bore 130 can be generally conical in form, with an included angle of approximately 10 degrees in some configurations. Regardless, the bore 130 can have a curvilinear shape in transverse cross-section (best shown in FIG. 4E) that corresponds with surface features or shapes of the tool interface end (not shown) as described below. For example, relative to the cross-section of FIG. 4E, an interior surface 136 of the plunger 110 otherwise defining the bore 130 can include opposing flattened faces 138a, 138b and opposing curved or arcuate faces 140a, 140b. While two of the flattened faces 138a, 138b and two of the arcuate faces 140a, 140b are shown, any other number, either lesser or greater, is also acceptable. As made clear below, the curvilinear shape defined by the interior surface 136 corresponds with an exterior shape provided by the tool interface end. As best shown in FIG. 4A, guide slots 141 are optionally formed at the leading end 132 at locations aligned with the flattened faces 138a, 138b providing a user with a visual guide as to the location of the flattened faces 138a, 138b.

Figure 4E:
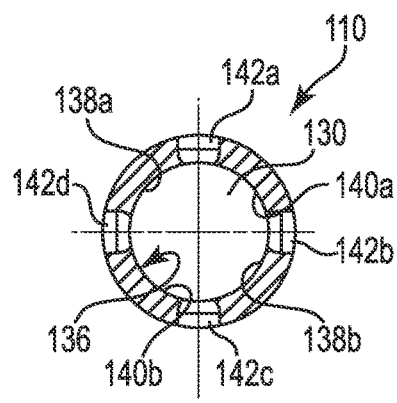
FIG. 4E is a transverse cross-sectional view of the plunger of FIG. 4A.
Figure 4F:
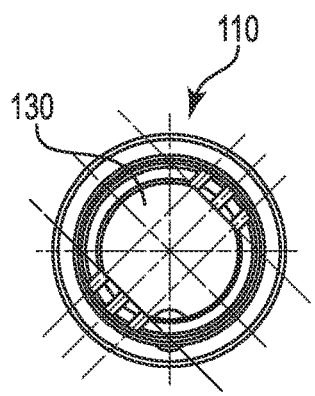
FIG. 4F is a front end view of the plunger of FIG. 4A.

FIG. 4E best illustrates holes 142a-142d extending radially through a thickness of the plunger 110 and open to the bore 130. The holes 142a-142 are sized and shaped to slidably receive a corresponding one of the balls 112 (one of which is shown in phantom in FIG. 4E). The holes 142a-142d can be longitudinally aligned, and are preferably located proximate the leading end 132. A size and shape of the holes 142a-142d permits a portion of the corresponding ball 112 to protrude into bore 130, yet prevents the ball 112 from passing entirely through the respective hole 142a-142d. While four of the holes 142a-142d are shown, any other number, either greater or lesser, is also acceptable, and corresponds with the number of balls 112. With the one embodiment of FIG. 4E, the holes 142a-142d are located along the arcuate faces 140a, 140b, with each hole 142a-142b positioned immediately adjacent a corner defined between one of the flattened faces 138a, 138b and a corresponding one of the arcuate faces 140a, 140b.

The plunger 110 forms a circumferential slot 150 adjacent the trailing end 134. The slot 150 is open to an exterior of the plunger 110, and is defined by opposing side walls 152a, 152b. For reasons made clear below, the slot 150 is sized and shaped to slidably receive the pins 120 (FIG. 3A).

Returning to FIG. 3D, the balls 112 are configured to be received within a corresponding one of the plunger holes 140a-140d, and are formed of a hardened material. In some constructions, the balls 112 can be formed of an electrically non-conductive material (e.g., ceramic) to electrically isolate the plunger 110 from other components of the tool connecter assembly 54. Alternatively, other hardened materials such as steel are also acceptable.

The collar 114 is a generally tubular body, forming a central passage 160 sized to be received over the plunger 110. The collar 114 can be viewed as defining a trailing region 162, an intermediate region 164 and a leading region 166. The trailing region 162 forms a radially extending flange 168. Further, the trailing region is configured for mounting to the drive shaft 84, and in particular the distal region 90 of the drive shaft 84. For example, the collar trailing region 162 and the drive shaft distal region 90 can form complimentary threads as shown. Other configurations for mounting the collar 114 to the drive shaft 84 are also envisioned that may or may not entail a threaded connection, and may or may not include additional components.

The intermediate region 164 extends from the trailing region 162 and defines a receiving surface 170. The receiving surface 170 is radially offset from the flange 168 and is configured to receive the spring 118 as described below. Further, one or more troughs 172 are formed through a thickness of the intermediate region, each sized to slidably receive a corresponding one of the pins 120.

The leading region 166 extends from the intermediate region 164 and terminates at a leading end 174. An interior face 176 of the collar 114 (otherwise defining the passage 160) tapers in diameter to the leading end 174. At least the leading region 166 is radially resilient, capable of repeatedly being radially compressed (i.e., to the diameter reflected in FIG. 3D), and in some embodiments exhibits a radially outward bias. For example, when a compressive force applied to the leading region 166 (for example by the sleeve 116) is removed, the leading region 166 self-expands radially outwardly. In some constructions, this resilient bias is created by forming the leading region 166 as series of aligned spring arms. The interior face 176 is configured to interface with the balls 112. Further, a groove 178 is formed along the exterior face of the leading region 166 and is configured to selectively receive a corresponding feature of the sleeve 116 for reasons made clear below.

The sleeve 116 is configured to be slidably received over the collar 114, and defines trailing and leading portions 180, 182 along with a central passageway 184. A diameter of the passageway 184 along the trailing portion 180 is greater than a diameter along the leading portion 182, and is generally commensurate with an outer diameter of the flange 168. Upon final assembly, a gap is formed between the trailing portion 180 and the collar receiving surface 170, sized to maintain the spring 116. An abutment surface 186 is defined at the transition to the leading portion 182.

The leading portion 182 extends from the trailing portion 180 and terminates at an end 190. The passageway 184 can have a uniform diameter along the leading portion 182 for slidably interfacing with the collar 114. One or more holes 192 are formed through a thickness of the leading portion 182, sized and shaped to receive a corresponding one of the pins 120.

The spring 118 can be a helical compression-type spring, and is sized to be received over the collar 114. As explained below, upon final assembly, the spring 118 establishes a biasing force on the sleeve 116 relative to the collar 114. Alternatively, other components or mechanisms can be employed to generate the desired biasing force that may or may not include a spring.

The cover 122 is configured to be received over the sleeve 116 and can assume a variety of shapes and constructions. In some embodiments, the cover 122 and the sleeve 116 have the complimentary configurations shown such that the cover 122 is frictionally locked to the sleeve 116 upon final assembly (e.g., a snap fit).

Construction of the tool connector assembly 54 includes mounting the collar 114 to the drive shaft 84. The balls 112 are placed into respective ones of the plunger holes 142a-142d (FIG. 4E), and the plunger 110 is disposed within the collar passage 160, with the slot 150 longitudinally aligned with the collar toughs 172. The spring 118 is disposed over the collar 114, bearing against the flange 168. The sleeve 116 is assembled over the collar 114, capturing the spring 118 between the flange 168 and the abutment surface 186. Further, the sleeve holes 192 are aligned with the collar troughs 172. In this aligned position, respective ones of the pins 120 are inserted into a corresponding one of the holes 192, through the corresponding trough 172, and into the plunger slot 150. Once inserted, a shank 200 of each of the pins 120 projects into the plunger slot 150, whereas a head 202 is seated within the sleeve hole 192. With this arrangement, the pins 120 slidably connect or capture the sleeve 116 relative to the collar 114, and the collar 114 relative to the plunger 110. Finally, the cover 122 is assembled over the sleeve 116 to capture the pins 120.

Figure 3D:
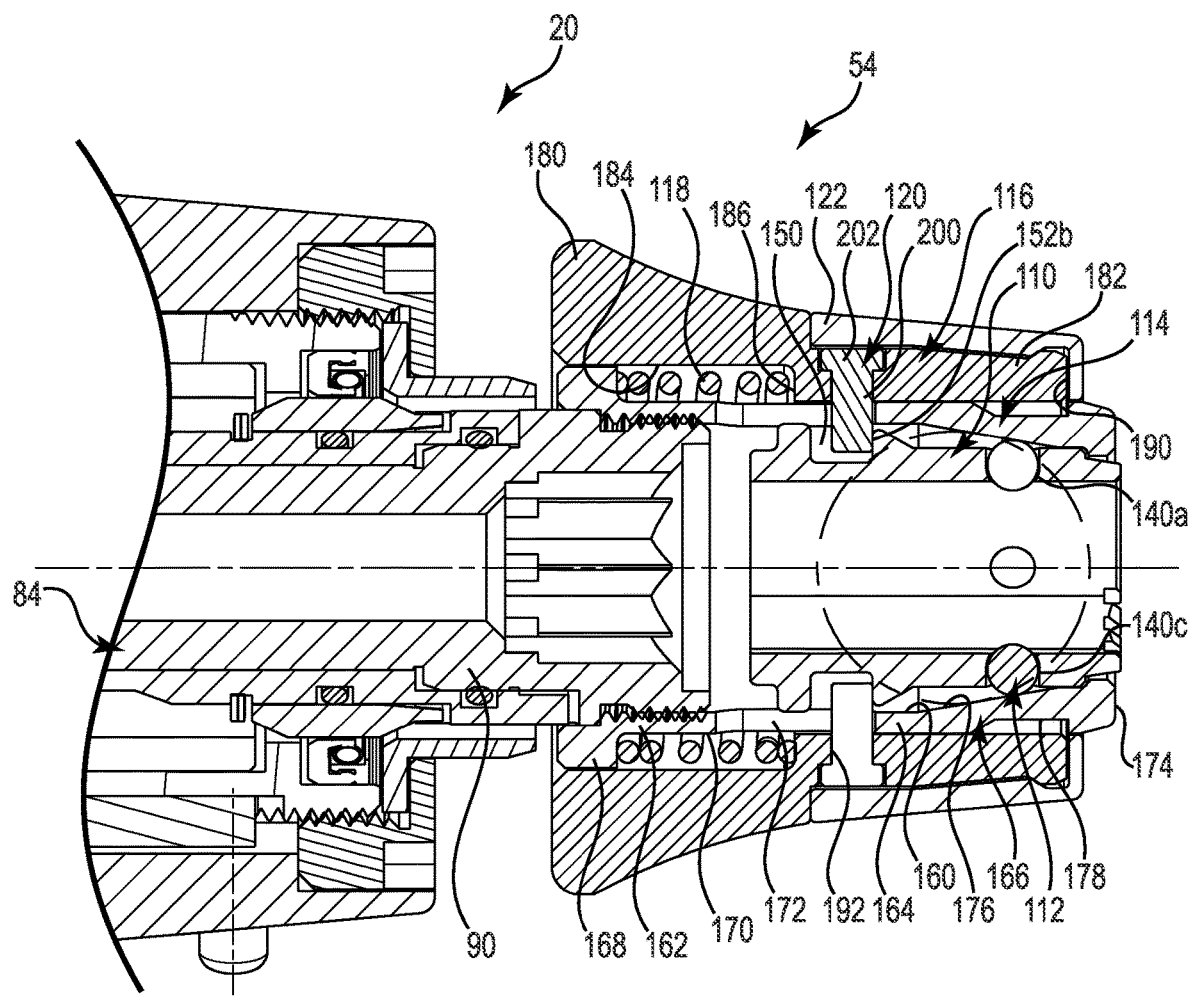
FIG. 3D is an enlarged view of a portion of the handpiece of FIG. 3A and illustrating a tool connector assembly of the handpiece.

The spring 118 biases the tool connector assembly 54 to the locked state reflected in FIG. 3D. In particular, because the collar 114 is longitudinally fixed to the drive shaft 84 and the spring 118 bears against the collar flange 168 and the sleeve abutment surface 186, the spring 118 biases the sleeve 116 distally relative to the collar 114. The pins 120 limit a forward or distal position of the sleeve 116 relative to the collar 114 and the plunger 110, bearing against the plunger side wall 152b in the locked state. In this forward position of the sleeve 116, the sleeve leading portion 182 bears against the collar leading region 166, radially compressing the collar interior face 176 against the balls 112. The balls 112, in turn, are forced into the plunger bore 130 to frictionally engage an object (e.g., tool interface end) inserted therein.

The balls 112 can be released from the plunger bore 130 by transitioning the tool connector assembly 54 to a released state, including manually retracting the sleeve 116 relative to the collar 114. A pushing force sufficient to overcome a force of the spring 118 is applied to the sleeve 116, causing the sleeve 116 to slide proximally along the collar 114. With this proximal movement, the sleeve leading portion 182 is withdrawn from over the collar leading region 166, allowing the collar leading region 166 to radially expand out of rigid engagement with the balls 112. The radially outward expansion of the collar leading region 166 can be enhanced by the sleeve end 190 being received within the collar groove 178. Once the inward bias on the balls 112 is removed, an object previously engaged by the balls 112 can readily be removed from the tool connector assembly 54.

Surgical Tools

The handpiece 20 (FIG. 1) can be used to drive or otherwise interface with a plethora of currently available, or in the future developed, surgical tools 30. Non-limiting examples of tools 30 envisioned by the pending application include drills, taps, drivers, reduction nut drivers, torque multipliers, post cutters, rod cutters, set-screw-break-off tools, resectors, debriders, burrs, etc.

Figure 5A:
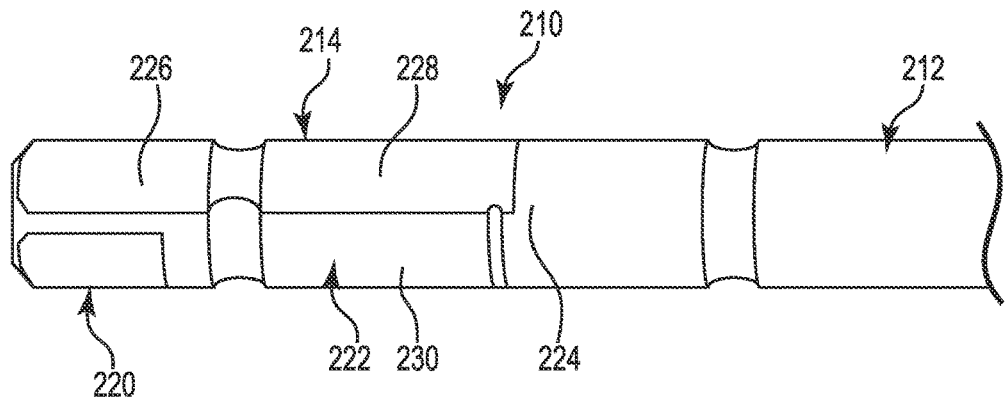
FIG. 5A is a perspective view of a portion of a surgical tool in accordance with principles of the present disclosure and useful with the system of FIG. 1.
Figure 5B:
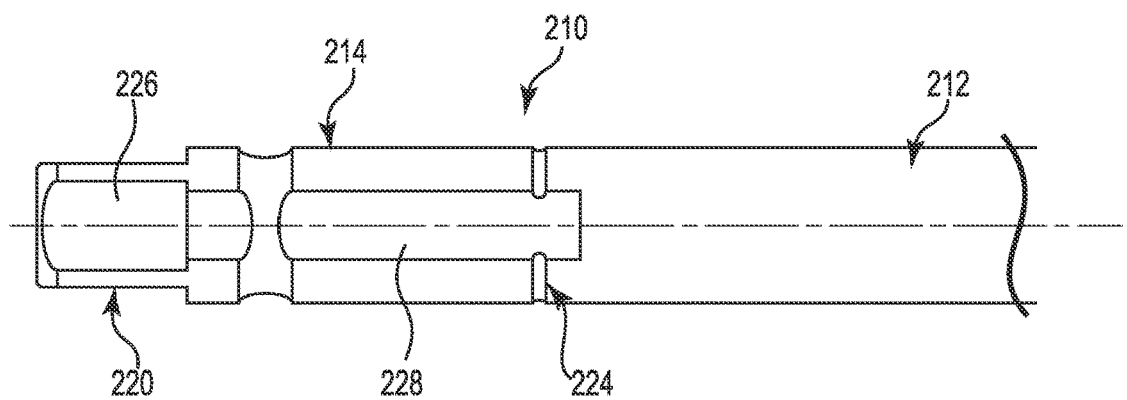
FIG. 5B is a side view of the tool of FIG. 5A.
Figure 5C:
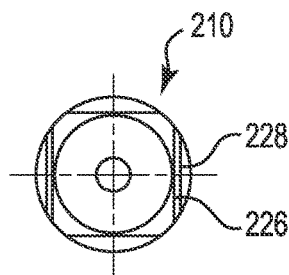
FIG. 5C is an end view of the tool of FIG. 5A.
Figure 5D:
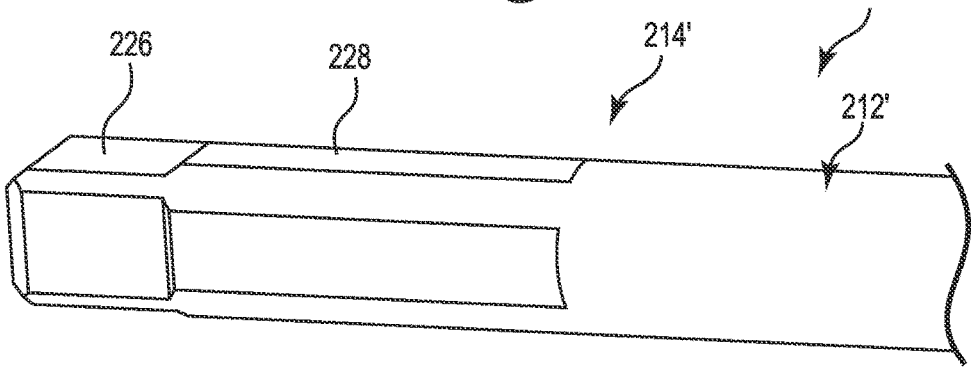
FIG. 5D is a perspective view of a portion of another surgical tool in accordance with principles of the present disclosure and useful with the system of FIG. 1.

As mentioned above, a size and shape of the plunger bore 130 (e.g., the flattened surfaces 138a, 138b of FIG. 4E) correspond with a size and shape of an interface end of tool to be used with the handpiece 20 in some embodiments. For example, FIGS. 5A-5C illustrate a portions of rotary-type surgical tools 210, 210' useful with handpieces of the present disclosure. The tool 210 generally includes a tool shaft 212 forming or defining a handpiece interface end or end section 214. The interface end section 214 includes or defines a post 220, an engagement portion 222 and a shoulder 224. The post 220 is configured for connection to the drive shaft engagement surface 94 (FIG. 3A, and thus can form two or more flattened surfaces 226. The post 220 has an outer diameter/outer dimension less than that of a remainder of the tool shaft 212 at least along the interface end section 214. The engagement portion 222 is sized and shaped in accordance with the plunger bore 130, and thus forms or defines exterior flats 228 circumferentially separated by curved surfaces 230. While tool 210 may comprise a conventional interface end 214 where flats 228 terminate at a shoulder 224, tool 210 may nevertheless interact with plunger 110 of the present disclosure as described below with reference to FIG. 6. FIG. 5D illustrates an alternative embodiment of another tool 210' having handpiece interface end section 214'. Tool 210' includes two or more flattened surfaces 226, 228. Flats 226, 228 may be circumferentially separated by curved surfaces 230 as with tool 210. Unlike 210 however, tool 210' may advantageously include no detents, grooves, indentations or other geometry, such as a shoulder, 224, generally forming a portion projecting inwardly from the surface of the tool 210' or tool interface end 214'. Such detents, grooves, indentations etc., as commonly known, may be configured for interaction with a handpiece or powered surgical instrument for coupling the tool to the instrument. In contrast, with the construction of handpiece 20 and particularly tool 210', the tool 210' or tool interface end 214' may be considered a "bare" shaft. With this configuration, tool 210' may beneficially interact with the plunger 110 whereby the plunger 110 is able to secure the tool shaft 212 at flat surfaces (e.g., 226, 228) upon initial engagement with the balls 112 as described in detail below.

Providing a bare shaft (and/or interface end 214') such as described may also advantageously result in more economical design and manufacturability of a tool (e.g., 210'). In some non-limiting embodiments, the tool shaft 212, 212' has a diameter of approximately 5/16 inch and the flats 228 measure approximately 7 mm across the flats 228. While the tool 210' is shown as having four of the flats 228, a lesser or greater number is also acceptable (e.g., two of the flats 228). It is to be understood that the interface end 214' may be included on any of the types of tools described or referred to herein.

Figure 6:
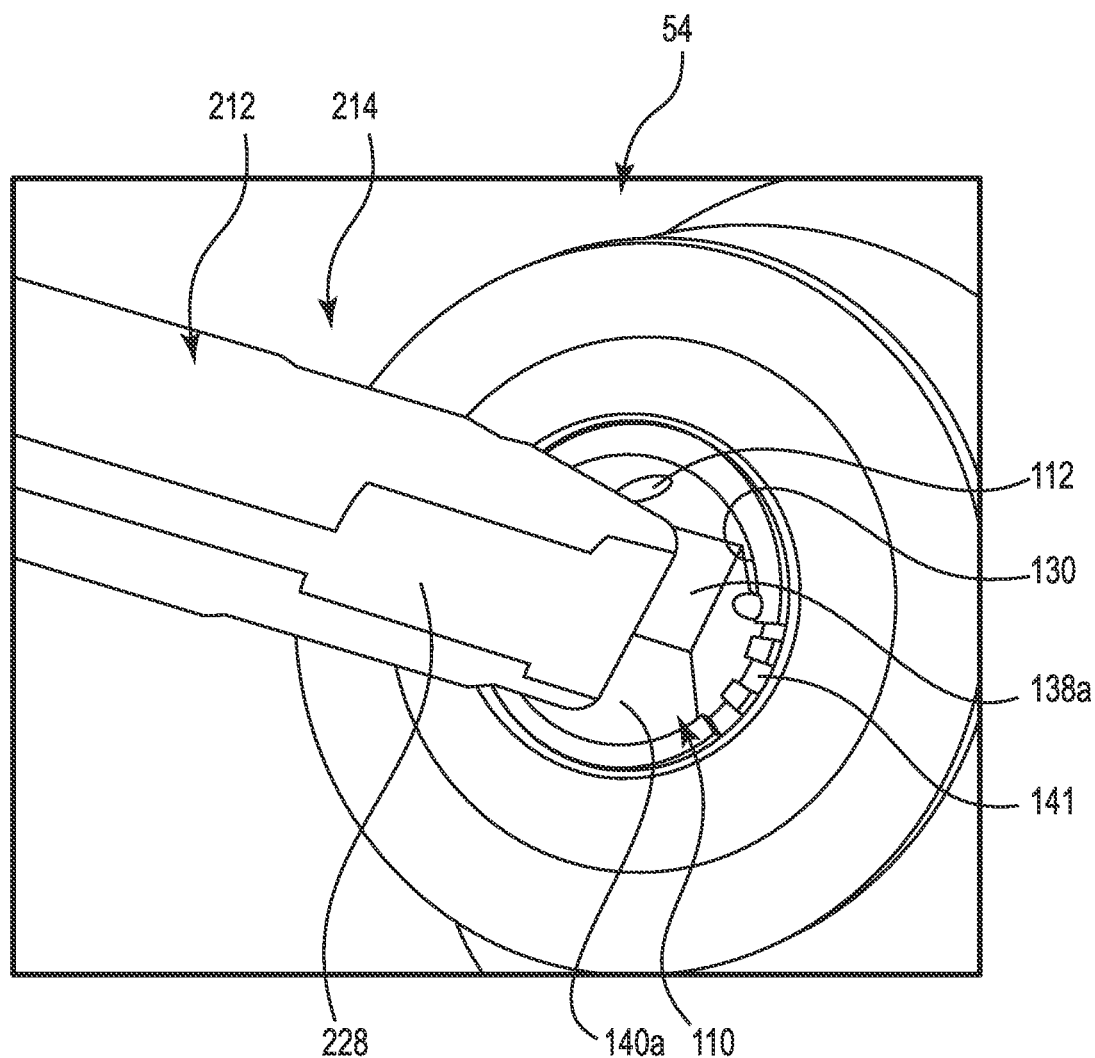
FIG. 6 is an enlarged perspective view illustrating mounting of the tool of FIG. 5A with the tool connector assembly of FIG. 3D.

FIG. 6 depicts a relationship between the tool interface end section 214 and the plunger 110. In the view, the tool interface end section 214 is configured to have two of the flats 228 and is poised for insertion into the plunger bore 130. With additional reference to FIGS. 4E and 5B, the flats 228 are aligned with respective ones of the flattened faces 138a, 138b. The guide slots 141 on the plunger 110 visually assist the user in identifying a location of the flattened faces 138a, 138b. As the tool interface end section 214 is inserted into the plunger bore 130, the flats 228 slide along the flattened faces 138a, 138b (and the curved surfaces slide along the arcuate faces 140a, 140b). Once the post 220 is engaged by the drive shaft 84 (FIG. 3A), insertion is complete and the tool connector assembly 54 is allowed to transition to the locked state described above. In the locked state, the balls 112 apply a radially inward force onto the engagement portion 222, frictionally securing the tool shaft 212 to the plunger 110, with the balls 112 effectively being wedged between the collar 114 (FIG. 3D) and the tool shaft 212. With this approach, the tool connector assembly 54 is beneficially able to retain a "bare" tool shaft (i.e., no detent or other geometry is required on the tool shaft 212). This provides a unique safety feature due to the ability to secure the tool shaft 212 upon initial engagement with the balls 112.

Trigger Assembly

Returning to FIGS. 3A and 3B, the trigger assembly 56 is generally configured to prompt operation of the motor 80 (and thus rotation of the drive shaft 84 and a tool assembled thereto) at a variable speed desired by a user. As a point of reference, in some embodiments the trigger assembly 56 is not directly connected to the motor 80, but instead generates or signals information to the controller 24 (FIG. 1) indicative of an action desired by a user otherwise interfacing with the trigger assembly 56, with the controller 24, in turn, prompting or powering operation of the motor 80 in response to the received information.

Figure 7:
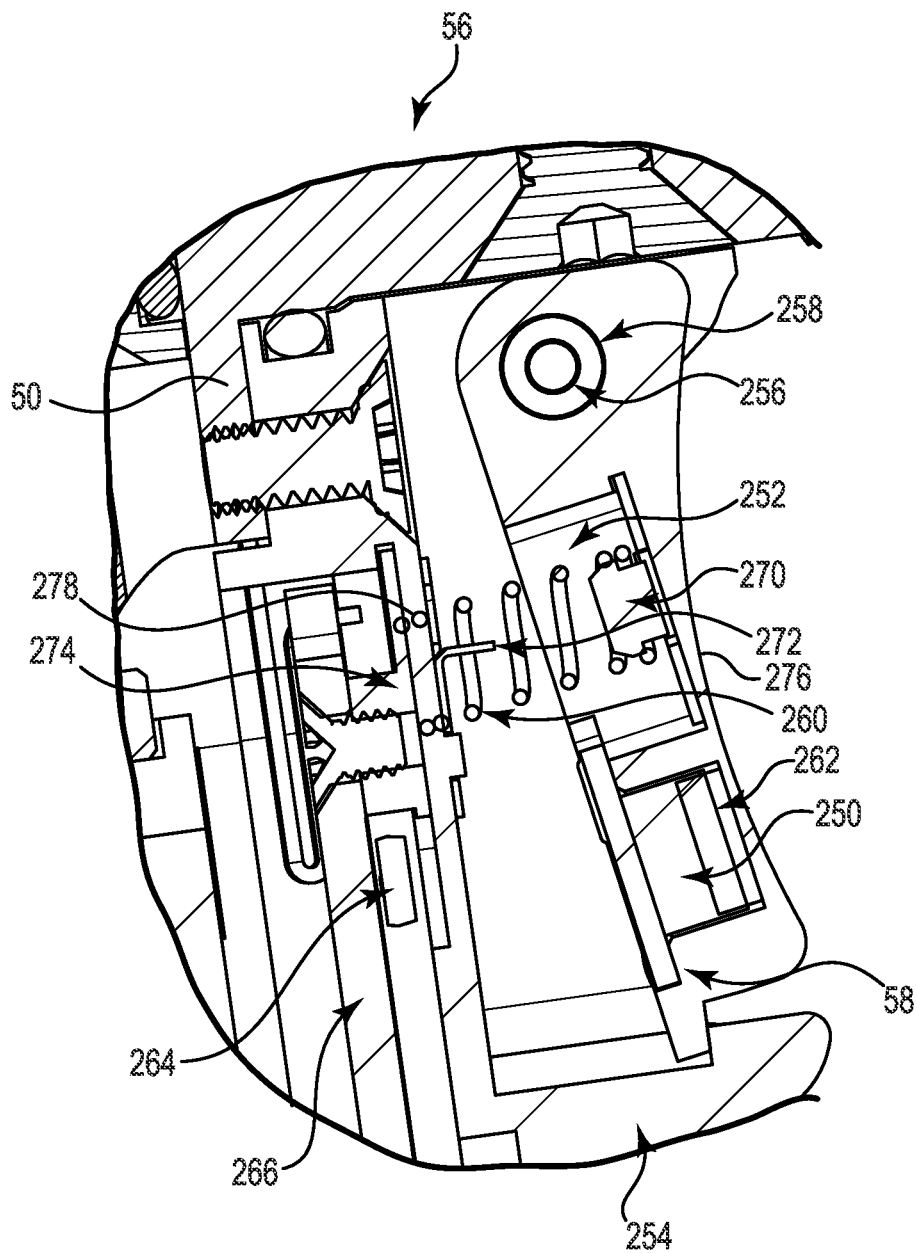
FIG. 7 is an enlarged view of a portion of the handpiece of FIG. 3A, illustrating a trigger assembly of the handpiece.

As shown in greater detail in FIG. 7, the trigger assembly 56 includes the trigger 58, a trigger position sub-assembly 250 (referenced generally), and a capacitive switch sub-assembly 252 (referenced generally). In general terms, a position of the trigger 58 relative to the grip 50 is sensed by the trigger position sub-assembly 250, with the trigger position sub-assembly 250 generating a signal indicative of the sensed position to the controller 24 (FIG. 1). As the trigger 58 is caused to move relative to the grip 50, for example pressing of the trigger 58 by a user's finger, the controller 24 correlates the changing position information from the trigger position sub-assembly 252 with a corresponding motor drive speed or rate and prompts or powers the motor 80 (FIG. 3A) to operate at this determined rate. The capacitive switch sub-assembly 252 signals information to the controller 24 indicative of a user's finger being in contact with (or not in contact with) the trigger 58. The capacitive switch sub-assembly 252 thus serves as a safety stop device, with the controller 24 programmed to automatically stop operation of the motor 24 when the capacitive switch sub-assembly 252 indicates that the user's finger is not in contact with the trigger 58.

The trigger 58 can assume a variety of forms conducive to ergonomically-correct interface by a user's finger, and can be made of a polymeric material for reasons made clear below. In some embodiments, the trigger 58 is carried by a bulkhead 254 component of the trigger assembly 56 that in turn is mounted to the grip 50. Alternatively, the trigger 58 can be assembled directly to the grip 50. Regardless, the trigger 58 is pivotably maintained relative to the grip 50 by a hinge pin 256, and is rotatable about an axis defined by the hinge pin 256. Optionally, a low-friction, durable, high temperature thermoplastic sleeve 258 surrounds the hinge pin 256 to provide reliable operation of the trigger 58 throughout the life of the handpiece 20, even when contaminated with tissue and debris.

The trigger 58 can be biased to the illustrated normal rotational position relative to the grip 50 by a spring 260. The spring 260 is disposed between the trigger 58 and the bulkhead 254, and forces the trigger 58 to the "stop" position shown. A reaction force generated by the spring 260 is within the biometric limits of the applicable user population (i.e., the spring bias can be overcome by a squeezing force applied to the trigger 58 via the index finger of a user's hand otherwise grasping the grip 50).

The trigger position sub-assembly 250 can assume a variety of forms conducive for generating a signal indicative of a rotational position of the trigger 58 relative to the grip 50, and in some embodiments includes a magnet 262, a Hall sensor 264 and a printed circuit board (PCB) 266. The magnet 262 is made from a rare earth material, and is fixed to the trigger 58. The magnet 262 provides a static magnetic flux array. The Hall sensor 264 is maintained at a fixed location relative to the trigger 58, and is adapted to sense the flux density of the magnet 262 and to generate an electrical signal proportional to the sensed flux density. Thus, as the trigger 58 moves, the magnetic flux density sensed by the Hall sensor 264 changes. The PCB 266 carries or is connected to the Hall sensor 264, and provides circuitry (not shown) delivering a signal from the Hall sensor 264 to other wiring (not shown) carried by the cabling 64 (FIG. 2A) and ultimately to the controller 24 (FIG. 1). The Hall sensor 264 and the PCB 266 can be located "behind" or within the bulkhead 254 (or otherwise within the grip 50), providing a liquid seal. The trigger 58, the hinge pin 256, the spring 260, and the magnet 262 are located outside of the sealed grip 50 and are easily cleaned (e.g., exposed to autoclave steam and cleaning agents).

In some embodiments, an additional, environmental Hall sensor 268 (FIG. 3A) is incorporated to reduce motor magnetic field interference with the trigger position Hall sensor 264. With this optional construction, the controller 24 (FIG. 1) is programmed to subtract the environmental Hall sensor's 268 voltage output from the trigger position Hall sensor's 264 output, greatly reducing motor magnetic field interference of the position sub-assembly circuit 266 and allowing smoother speed control. The environmental Hall sensor 268 is located in a fixed position some distance from the trigger position Hall sensor 264 in order to minimize signal interference from the trigger magnet 262.

The capacitive switch sub-assembly 252 can assume a variety of forms capable of sensing presence of a user's finger on the trigger 58, and in some embodiments includes a trigger contact plate 270, the spring 260, an outer bulkhead contact plate 272, an inner bulkhead contact plate 274 (referenced generally), and the PCB 266.

The trigger contact plate 270 is an electrically conductive capacitive pad mounted within the trigger 58. As shown, the trigger contact plate 270 is located in close proximity to an exterior face 276 of the trigger 58, and thus in close proximity to an expected location of a user's finger when the user is otherwise intentionally actuating or touching the trigger 58.

The outer and inner bulkhead plates 272, 274 are also electrically conductive capacitive pads, and are mounted at opposite sides of the bulkhead 254. The bulkhead 254 can be a polymeric material, with the bulkhead plates 272, 274 spanning the polymeric bulkhead 254. Thus, the inner bulkhead plate 274 is within the liquid sealed grip 50. Further, the inner bulkhead plate 274 is electrically connected to circuitry (not shown) carried by the PCB 266 that in turn delivers a signal from the inner bulkhead plate 274 to other wiring (not shown) carried by the cabling 64 (FIG. 2A) and ultimately to the controller 24 (FIG. 1).

By forming the three contact plates 270, 272, 274 as electrically conductive capacitive pads, two capacitors in series are created. The spring 260 serves to conduct capacitive changes between the trigger contact plate 270 and the outer bulkhead contact plate 272, and the bulkhead plates 272, 274 spanning the bulkhead 254 effectively provide direct continuity between the spring 260 and the PCB 266.

With the above construction, an electrical charge (or absence thereof) at the trigger exterior face 276 as caused by a user's finger being in contact with the trigger 58 is "sensed" as a change in capacitance by the plates 270, 272 and the spring 260. The capacitive switch sub-assembly 252 sends a signal to the controller 24 (FIG. 1) as a function of this changing capacitance, and is thus indicative of the user's finger being in contact, or not in contact, with the trigger 58. The controller 24 can be programmed to designate the determined absence of the user's finger on the trigger 58 as an indication that the user does not want the motor 80 (FIG. 3A) to operate, and thus immediately shuts of the motor 80. In other words, the controller 24 can be programmed to stop the motor 80 when the capacitive switch sub-assembly 252 signal is equivalent to the user's finger being removed from the trigger 58. Thus, the capacitive switch sub-assembly 252 serves as a safety stop. The trigger capacitance is conveyed to the PCB 266 (and thus to the controller 24) via electrically conductive components and a single or plurality of conductive and/or capacitive plates, and optionally includes the spring 260. The capacitive plate(s) (e.g., the plates 270-274) can span a sealed pressure vessel, precluding the need for a pass-thru seal (i.e., eliminating a potential leak path).

In some embodiments, and for added safety, the controller 24 (FIG. 1) can be programmed such that signals from the trigger position sub-assembly 250 and the capacitive switch sub-assembly 252 are inverted. For example, the controller 24 can be programmed such that a valid "run" condition (e.g., the motor 80 is activated) requires one of the two signals to have an increasing voltage, while the other signal has a decreasing voltage. If these conditions are not met within a specified time, the controller 24 precludes operation of the motor 80. Alternatively, the controller 24 can be programmed to interpret, and act upon, signals from the trigger position sub-assembly 250 and the capacitive switch sub-assembly 252 in a wide variety of other manners that may or may not include correlating information from one signal with information from the other signal.

Mode Selection Assembly

Returning to FIGS. 3A and 3B, the mode selection assembly 60 is generally configured to facilitate user selection of a desired operational mode or rotational direction and to signal the selected mode/direction to the controller 24 (FIG. 1). The controller 24, in turn, is programmed to prompt operation of the motor 80 in accordance with the selected mode/direction. With this in mind, in some embodiments the mode selection assembly 60 includes the collar 62, a ring 300, a magnet 302, one or more Hall sensors 304, and a printed circuit board (PCB) 306. In general terms, the ring 300 carries the magnet 302, and is mounted to the collar 62. The collar 62, in turn, is rotatably coupled to the housing 40 at or along the nose 52 and is rotatable about the axis of shaft 84. The Hall sensor(s) 304 detect a change in location of the magnet 302 with rotation of the collar 62, and signal corresponding information to the controller 24 via the PCB 306.

The collar 62 can assume a variety of constructions and in some embodiments is configured to facilitate ergonomic interface therewith by a finger of a user's hand otherwise grasping the grip 50. For example, the collar 62 can be constructed for assembly to the housing 40 immediately adjacent or "above" the trigger 58. At this location, a finger (e.g., index finger) of the user otherwise employed to manipulate the trigger 58 can also interface with the collar 62. As further illustrated in FIGS. 2A and 2B, the collar 62 can carry or form wings 310, 312 that project in a generally radial fashion from a base 314. Upon final assembly, the wings 310, 312 are conveniently located to receive a user's finger, facilitating user-caused rotation of the collar 62 in a desired direction (e.g., the user's finger presses against the first wing 310 to rotate the collar 62 in a first direction, and against the second wing 312 to rotate the collar 62 in the opposite direction).

Figure 8:
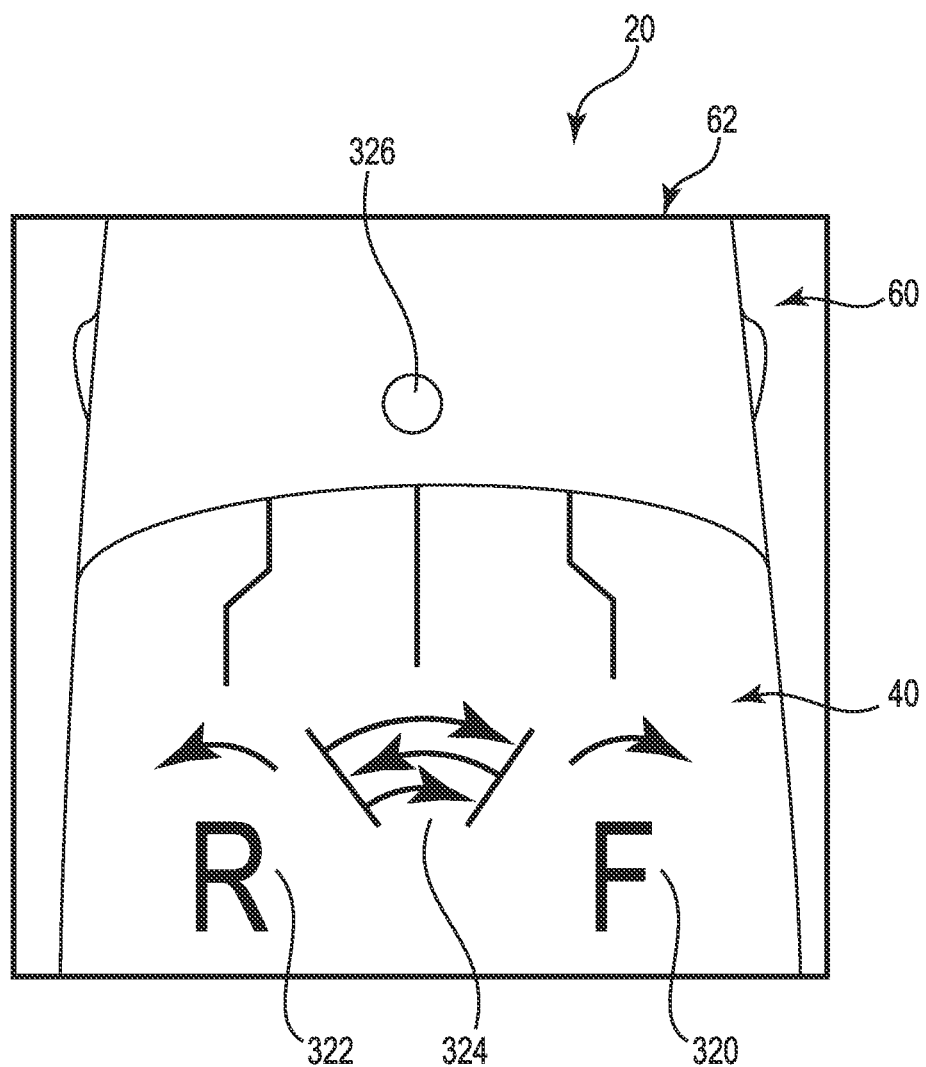
FIG. 8 is an enlarged top view of a portion of the handpiece of FIG. 2A.

As further reflected in FIG. 8, the housing 40 can display indicia that visually correlates a rotational position of the collar 62 relative to the housing 40 with a particular mode of operation or rotational direction. For example, the indicia can include "forward" indicia 320 (e.g., clockwise rotation direction), "reverse" indicia 322 (e.g., counterclockwise rotation direction), and "oscillation" indicia 324 (e.g., oscillating mode of operation). The collar 62, in turn, carries or displays selector indicia 326. As made clear below, the controller 24 (FIG. 1) is programmed to operate the motor 80 (FIG. 3A) in a forward rotation direction mode when signaled with information indicative of the selector indicia 326 being aligned with the forward indicia 320; in a reverse rotation direction mode when signaled with information indicative of the selector indicia 326 being aligned with the reverse indicia 322; and in an oscillating mode when signaled with information of the selector indicia 326 being aligned with the oscillation indicia 324. The mode selection assembly 60 can include additional components that provide mechanical control over rotational movement of the collar 62 relative to the housing 40, for example as described below in connection with the ring 300.

With specific reference to FIGS. 3A and 3B, the ring 300 is mounted to the collar 62, and is slidably received over the housing 40. The magnet(s) 302 are fixed relative to the ring 300 (e.g., the magnet(s) 302 can be embedded into the ring 300). Upon final assembly, then, the magnet(s) 302 are statically fixed relative to the collar 62 via the ring 300.

As mentioned above, the mode selection assembly 60 can include additional components that interface with the ring 300 and provide mechanical control over movement of the collar 62. For example, and as best shown in FIG. 3A, the ring 300 can form a slot 330 configured to slidably receive a pin 332 mounted to the housing 40. The pin 332 limits the travel of the ring 300, and thus of the collar 62, as it contacts the end of the slot 330. Further, the ring 300 can form depressions 334 (one of which is visible in FIG. 3A) configured to selectively receive a plunger device 336 assembled to the housing 40. The plunger device 336 can include a spring 338, a seat 340, and a ball 342. The ball 342 is carried by the seat 340 and is sized to be received within each of the depressions 334. The spring 338 biases the seat 340, and thus the ball 342, toward the ring 300. Finally, a location of each of the depressions 334 corresponds with a respective one of the operational modes. For example, when the collar 62 is arranged such that the collar selector indicia 326 (FIG. 8) is aligned with forward indicia 320 (FIG. 8), a first one of the depressions 334 will be aligned with the ball 342, and the ball 342 will be biased into engagement with the depression 334. Thus, the plunger device 336 in combination with the depressions 334 provides positive engagement of the collar 62 in each selected mode or operational direction, and can be made from metal to provide audible and tactile feedback. Additionally, though not explicitly shown in the drawings, the mode selection assembly 60 can include a coil compression spring that applies a force onto the ring 300 or the collar 62, biasing the collar 62 to the forward position when a finger force is removed from the collar 62.

The magnet(s) 302 are made from rare earth material and provide a static magnetic flux array. This array is static relative to the magnet 302, and the magnet 302 is fixed relative to the collar 62 via the ring 300. As the collar 62 rotates, the magnetic flux array rotates with the magnet 302.

The Hall sensor(s) 304 are mounted to the PCB 306 at a fixed location relative to the housing 40, and are configured to sense the flux density of the magnet(s) 302. An electrical signal generated by the Hall sensors 304 is proportional to the sensed flux density. The PCB 306 carries or is connected to the Hall sensors 304, and provides circuitry (not shown) delivering a signal from the Hall sensors 304 to other wiring (not shown) carried by the cabling 64 and ultimately to the controller 24 (FIG. 1).

Figure 9:
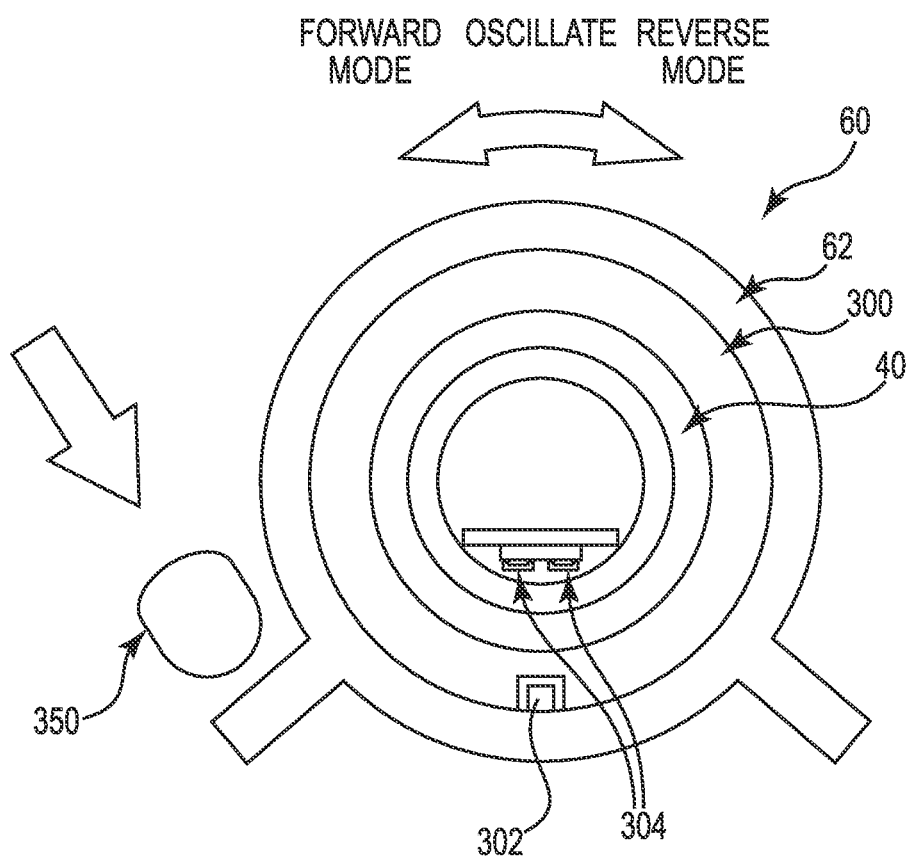
FIG. 9 is a schematic illustration of a mode selection assembly portion of the handpiece of FIG. 3A.

FIG. 9 schematically illustrates the mode selection assembly 60. The collar 62 rotates amongst three mode positions relative to the housing 40 via actuation by the user's index or other finger 350. The three modes, moving from full flexion of the user's index finger 350 to full extension of that finger 350 are: forward, oscillate and reverse. The collar 62 rotates via an index finger force appropriate to the applicable user biometrics. The Hall sensors 304 each generate an electrical signal proportional to the sensed flux density of the magnet 302 that in turn is a function of a rotational position of the collar 62. The controller 24 (FIG. 1) is programmed to interpret the so-generated signals in determining a mode or operational direction desired by the user, and then prompt the motor 80 (FIG. 3A) to operate in accordance with this selection.

In more general terms, the mode selection assembly 60 is configured to provide the rotatable collar 62 as an electromechanical switch within a reach of an index finger of a user's hand otherwise grasping the grip 50 (FIG. 2A). The assembly 60 provides feedback to the controller 24 (FIG. 1), such as motor/tool direction (e.g., forward, reverse, or oscillate), motor safety stop, reset a value within the controller 24, and/or activate, deactivate, or cycle amongst multiple handpieces electrically connected by the single controller 24. An arrangement of the magnet 302 (or an array of the magnets 302 fixed relative to each other) and a plurality of the Hall sensors 304 are fixed relative to each other in which the magnet/magnet array moves relative to the sensor/senor array by manual manipulation. Relative displacement is converted to voltage signals, which control a function within the controller 24. The relative motion can be a single rotation or translation, or more complex including up to rotation about three orthogonal axes and translation along three orthogonal axes.

Optionally, and for added safety, signals from the Hall sensors 304 can be individually inverted for forward and reverse directions. For example, in the forward state or mode, a first one of the Hall sensors 304 must exhibit high voltage while the second one of the Hall sensors 304 must exhibit low voltage; in the reverse state, the first Hall sensor 304 must exhibit low voltage while the second Hall sensor 304 must exhibit high voltage. With this approach, a single shorting event is unlikely to cause a forward "command" to be incorrectly signaled as a reverse "command" to the controller 24 (FIG. 1) (and vice-versa).

Motor Assembly

Returning to FIGS. 3A-3C, the motor 80 is provided as part of a motor assembly 380 that can further include an output shaft 382, end caps 384a, 384b, and wires 386a-386c. The motor 80 is a brushless electric motor configured to provide sufficient mechanical power to the output shaft 382. Hall sensors may optionally be present in the motor 80. The motor 80 is optionally connected to only three of the wires 386a-386c, one for each phase.

The output shaft 382 is rotatably driven by the motor 80. Gear teeth 388 can be formed directly into the output shaft 382 for interfacing with the gear train 82 and serving as a pinion as described below.

The end caps 384a, 384b seal the motor 80 from steam and steam condensate in combination with a mechanical shaft seal 390 and an injectable polymer sealant 392. Flat polymeric gaskets 394 can be provided that prevent the sealant 392 from contaminating ball bearings of the motor 80 and seal the motor mounting screw holes in the end caps 384a, 384b. The end caps 384a, 384b thus aid in sealing the motor 80 and provide locating features for the shaft seal 390, the sealant 392, and the gaskets 394.

Gear Train

Figure 10:
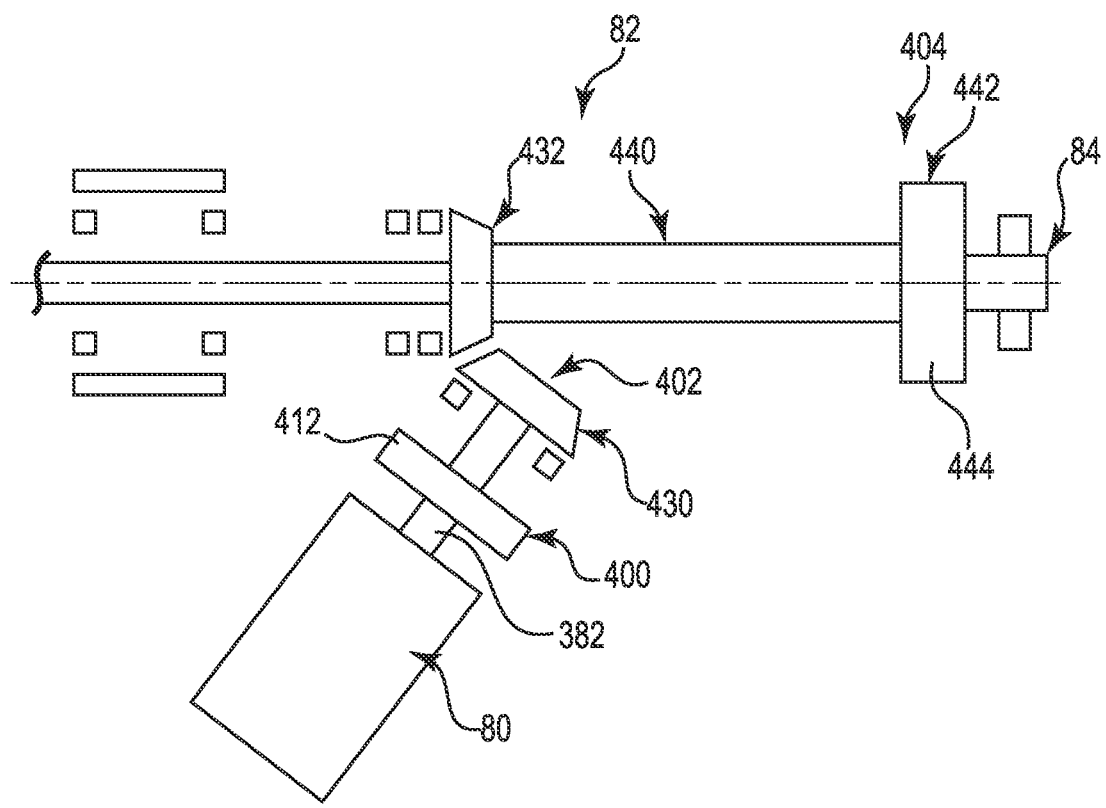
FIG. 10 is a schematic illustration of a gear train portion of the handpiece of FIG. 3A.

The gear train 82 can assume a wide variety of forms appropriate for transferring rotation of the motor output shaft 382 to the drive shaft 84. In one embodiment envisioned by the pending application, the gear train 82 is a gear reduction system that includes a first stage planetary set 400, a second stage bevel set 402, and a third stage planetary set 404. With additional reference to the simplified schematical illustration of FIG. 10, the stages 400-404 increase motor 80 torque to the required output shaft torque while meeting minimum output shaft 84 speed requirements.

The pinion 388 provided by the motor output shaft 382 serves as the sun gear of the first stage planetary set 400. The pinion/sun gear 388 threadably interfaces with planetary gears 410 otherwise maintained within an annulus gear 412 that serves as a carrier for the first stage 400. The pitch, reduction ratio, and material of the gears of the first stage 400 are selected to deliver high reduction and small size while maintaining tooth stress within acceptable levels.

A bevel pinion gear 430 of the second stage 402 engages directly with the carrier of the first stage 400. As a point of reference, the bevel pinion gear 430 does not rotate at the same speed as the motor output shaft 382. Teeth of a bevel gear 432 interface with teeth of the bevel pinion gear 430, with the bevel gear 432 serving as an output to the third stage 404. The pitch and reduction ratio, and materials of the second stage 402 are selected to deliver high reduction, small size while maintaining tooth stress within acceptable levels. Further, each of the bevel gears 430, 432 is supported by bearings capable of adequately reacting to radial and thrust loads experienced by the bevel gears 430, 432.

The third stage 404 includes a sun gear 440 that forms teeth functioning as a spline drive directly engaging the bevel gear 432. The sun gear 440 further forms part of a planetary gear assembly 442 having a carrier 444 that directly engages the drive shaft 84.

Stimulator Assembly

Figure 11:
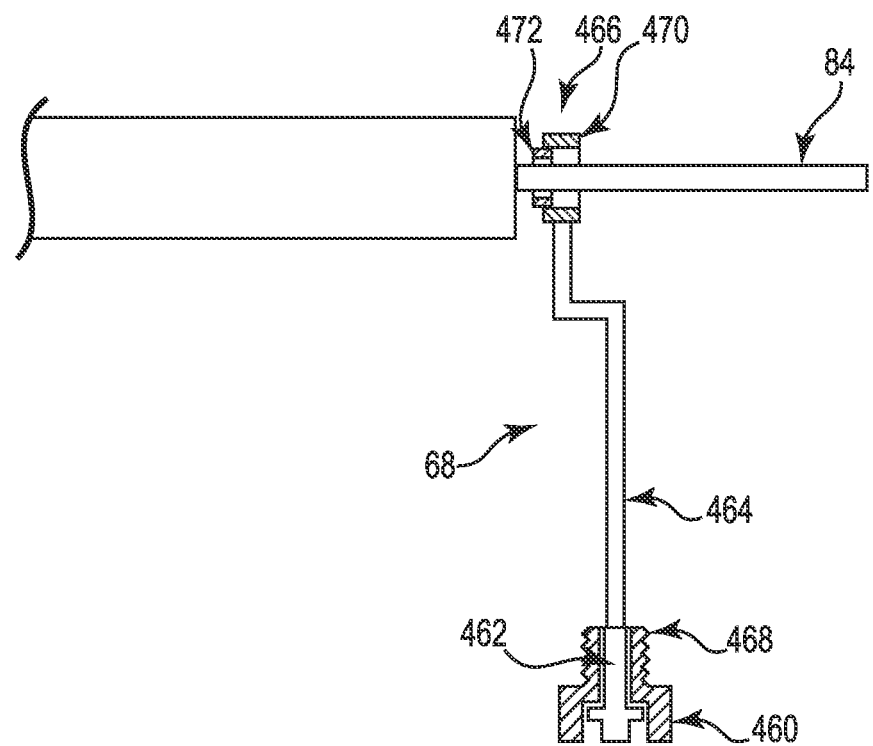
FIG. 11 is a schematic illustration of a stimulator assembly portion of the handpiece of FIG. 3A.

With specific reference to FIG. 3A, the stimulator assembly 68 is generally constructed to provide an electrical current stimulation path to the drive shaft 84, and thus to a surgical tool (not shown), mounted to the drive shaft 84. In some embodiments, and with additional reference to FIG. 11, the stimulator assembly 68 includes a shroud or port 460, a pin 462, wiring 464 (hidden in FIG. 3A), and a contact sub-assembly 466. The shroud 460 is configured for mounting to the housing 40 (e.g., via threads 468) and maintains the pin 462. The pin 462 is made of an electrically conductive metal such as brass. Conversely, the shroud 460 is constructed of a durable, high-temperature insulting material that protects the metal pin 462 and insulates the metal pin 462 from the housing 40. The shroud 460 and the pin 462 are shaped and sized to receive and electrically interface with a conventional input plug (not shown) from a separate stimulation power source.

The wiring 464 includes insulated wires that transmit stimulation energy from the pin 462 to the contact sub-assembly 466. The wires can be soldered directly to the pin 462 and the contact sub-assembly 466.

The contact sub-assembly 466 can assume various forms configured to transmit stimulation energy from the wiring 464 to the drive shaft 84. In one embodiment, the contact sub-assembly 466 includes a contact housing 470 and a slip ring 472. The slip ring 472 is constructed of an electrically conductive, corrosion and wear resistant metallic material (e.g., bronze), and is sized to be disposed over the drive shaft 84. The contact housing 470 retains the slip ring 472 and provides a solder cup for connection with the wiring 464.

With the above construction, the stimulator assembly 68 is capable of delivering adequate stimulation energy to the drive shaft 84. The so-provided stimulation energy is conducted from the drive shaft 84 to an electrically conductive tool mounted to the shaft 84 for performing various surgical protocols, such as nerve integrity monitoring (NIM). The stimulation energy can be provided to the tool whether the shaft 84 is rotating or stationary. While the handpiece 20 has been described as employing the slip ring 472 to deliver the stimulation energy to the drive shaft 84, electrical contact can be established with other constructions such a canted coil spring or a brush. Regardless, and as shown in the drawings, the drive shaft 84 is electrically isolated from other components of the handpiece 20 (apart from the contact sub-assembly 466) by polymeric or ceramic sheaths, tubes or bearings. Various other electrical isolation features in accordance with some embodiments are further shown in FIG. 12.

Figure 12:
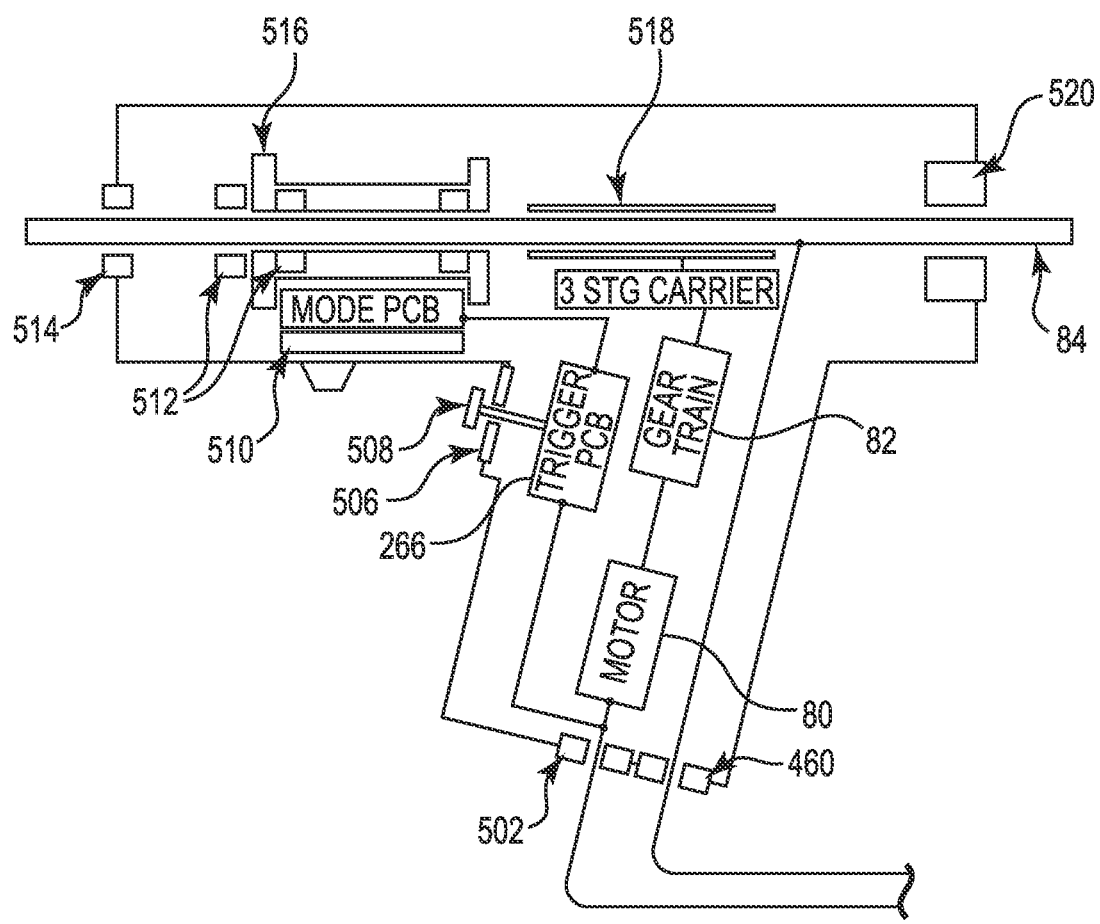
FIG. 12 is a schematic illustration of the handpiece of FIG. 3A and depicting electrical isolation of components thereof.

As schematically illustrated in FIG. 12, the handpiece 20 may include various insulators such as a cable insulator 502, a trigger insulator 508, an insulator 510 for insulating PCB 306, a shaft insulator 514, a bearing spacer insulator 516, a gear insulator 518, and an endcap insulator 520. Each of the insulators described above may be formed of various suitable materials, one non-limiting example being polyetheretherketone (PEEK).

Additional Optional Handpiece Features

With reference to FIG. 3A, the handpiece 20 can be configured for autoclave/steam sterilization (e.g., all exposed components are sufficiently robust to withstand repeated high pressure steam sterilization). A check valve assembly 480 can optionally be mounted to the housing 40, configured to provide fluid communication between an interior of the housing 40 and ambient air. The check valve assembly 480 is configured to assume an open state when subjected to sterilization conditions whereby an interior pressure of the housing 40 exceeds an external pressure acting on the housing 40 to allow evacuation of air from the housing 40. Examples of check valve assemblies useful with the present handpiece 20 can be found, for example, in U.S. patent application Ser. No. 13/419,129 entitled, "Check Valve Vented Sterilizable Powered Surgical Handpiece", incorporated by reference herein in its entirety.

The handpiece 20 is optionally configured to interact with an image guidance system. The handpiece 20 is thus optionally configured to receive an optional navigation adapter. For example, the nose 52 is sized and shaped to provide an interference fit with a component (e.g., O-ring) contained within the navigation adapter (e.g., available from Medtronic, Inc.) generating enough friction to prevent rotation of the navigation adapter.

a. The handpiece 20 is also optionally configured to include an electric ratcheting feature. For example, the electric ratchet features described in U.S. Patent Application Publication No. 2012-0274253 "Electric Ratchet for a Powered Screwdriver", hereby incorporated by reference in its entirety, may be useful with the present disclosure.

Controller

The controller 24 is a microprocessor based computer including associated memory and associated input/output circuitry. The entry device 26 and the display screen 28 can be housed with controller 24, or can be separate components. Further, the entry device 26 and the display screen 28 can be combined, such as with a graphic user interface or touch screen. In some embodiments, the controller 24 is an integrated power console available from Medtronic, Inc. of Minneapolis, MN under the trade name IPC®, and programmed (e.g., software) to interface with the handpiece 20 as described above.

As indicated by the above explanations, the controller 24 can be programmed to interface with the handpiece 20 for various operations, can receive input from a user and can provide real-time feedback to a user. For example, in some embodiments, the controller 24 is programmed to display applied torque on a graphic user interface based on motor current feedback. The controller 24 can limit torque rate of change over time based upon motor current feedback, and can detect screw, tool and/or bone failure by monitoring torque rate of change over time. Along these same lines, the controller 24 can be programmed to react to screw, tool, and/or bone failure by stopping the motor 80 (FIG. 3A) and/or controlling current delivered to the motor 80. The controller 24 can be programmed to display screw advancement/displacement on a graphic user interface based on motor position feedback and screw lead (thread pitch). The controller 24 can provide active braking when the safety stop (via the capacitive switch sub-assembly 252 (FIG. 3A)) is activated (e.g., the user's finger is removed from the trigger 58 (FIG. 3A)) by stopping the delivery of power to the motor 80. In conjunction with information received from the stimulation assembly 68 (FIG. 3A), the controller 24 can stop the motor 80 when the supplied stimulation energy reaches a threshold value. Also, the controller 24 can be programmed to provide motor over-temperature protection via an algorithm that estimates motor winding temperatures by integrating the square of the motor current over time. Furthermore, the algorithm can compensate for current losses due to winding resistance changes using the temperature estimate.

The rotary-type powered handpieces, and corresponding systems and methods of use, provide a marked improvement over previous design. Using just a single hand/finger, a surgeon is able to quickly select a desired operational direction and/or mode, as well as directly control a rate of rotation. These and other features described above are incorporated into a handpiece otherwise capable of operating at variable speeds of 0-250 rpm with a maximum torque in excess of 7 Nm.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

This disclosure describes a motor-driven powered screwdriver system with an electric ratchet. The system controls the motor to create a ratchet by preventing or limiting relative rotation of the powered driver and a driven screw in one direction, while permitting freewheel rotation in the other. Particularly, to drive a screw using the electric ratchet, the screwdriver system detects displacement of motor components and responds by powering the motor to limit or prevent further displacement. Accordingly, when motor displacement beings to occur as a result of manually applied torque, the motor is powered to offset the displacement effectively limiting the driver from slipping relative to the screw in one direction. However, the motor effectively permits freewheel rotation in the second direction. Accordingly, by rotating the whole driver relative to the driven screw, a user can ratchet and drive the screw to a desired depth and orientation. As used herein, freewheel rotation is intended to encompass at least two scenarios: First, freewheel rotation occurs when the motor is not powered to prevent motor displacement in the second, opposite direction; and second, freewheel rotation occurs when the motor is powered to offset drive train drag when the motor is rotated in the second opposite direction.

The powered screwdriver system is particularly well suited for surgical applications where the driver is used to drive bone screws, such as pedicle screws. The user can use the motor powered driver to drive the screw to near its desired depth. In order to reduce the risk of over tightening or over driving however, the user can stop conventional driving with the motor and use the driver as a ratchet to complete the screw implantation to the desired torque or depth. In addition, as some bone screws, such as some pedicle screws, spinal rods, cables, or other medical instrumentation, the electric ratchet allows the fine adjustment necessary for aligning the screw as desired without detaching the driver from the screw and without requiring a separate ratchet or manual screwdriver. This increases surgical efficiency and convenience for the surgeon. In addition, since the electric ratchet lacks large, heavy mechanical ratchet components, the resulting ratcheting screwdriver does not increase operator fatigue or potential operator injury. This may lead to more effective screw targeting and improved patient outcome.

Furthermore, because the electrical ratcheting system operates using motor control instead of bulky mechanical components, the systems disclosed herein achieve ratcheting operation without adding additional mass and weight. By avoiding the additional mass, the drivers disclosed herein do not have the extra inertia that comes from the mechanical systems, making the driver more efficient. This enables a compact size and minimizes driver weight, which are important benefits to an operating surgeon.

Figure 13:
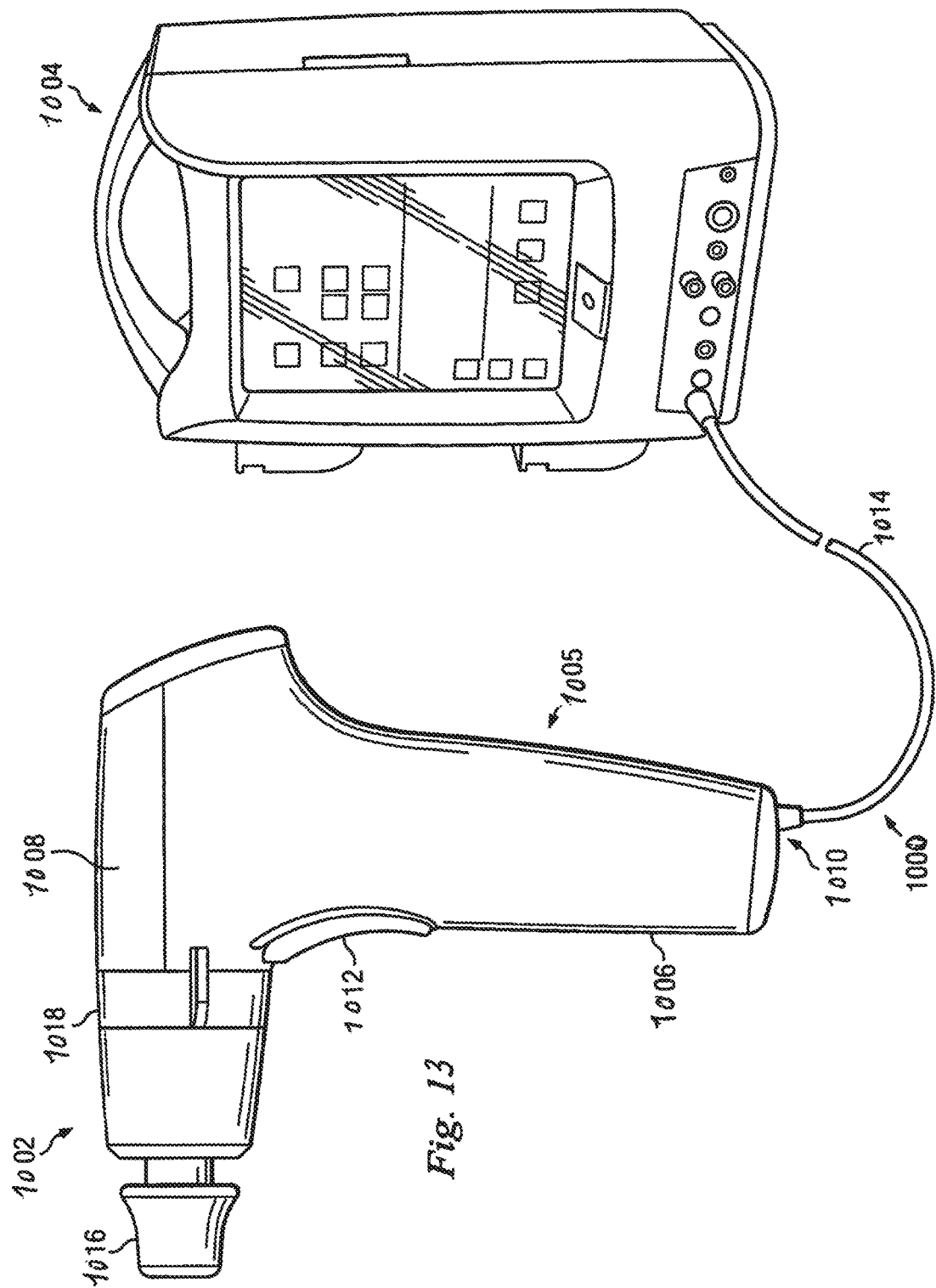
FIG. 13 is an illustration of an exemplary motor powered screwdriver system including a driver and a control console and provided with an electric ratchet in accordance with a first embodiment of the present disclosure.

FIG. 13 illustrates a powered screwdriver system 1000 according to an exemplary embodiment of the present invention. The system includes a motor powered driver 1002 and a control console 1004. The driver 1002 operates at variable rotational velocities to drive taps, drill bits, and surgical hardware, such as, for example, bone screws during a surgical procedure. In addition to performing these functions using motor power, the driver 1002 is configured with an electric ratchet. The driver 1002 includes an outer housing 1005 in the shape of a handle 1006 and a barrel 1008. Here, the handle 1006 extends from the barrel 1008 in a pistol-grip fashion for convenience and comfort of the user. The handle 1006 includes an electrical port 1010 and an input device, here shown as a trigger 1012. In some examples, the trigger 1012 includes a permanent magnet and a Hall effect sensor. In use, the magnetic field detected by the Hall effect sensor changes based on the relative position of the trigger 1012 and the proximity of the magnet within the trigger to the Hall effect sensor.

The barrel 108 includes a collet 1016 and a mode selector 1018. Other input devices, such a torque control level or limit, alignment elements, and other features also may be included. The collet 1016 is disposed at the working end of the driver 1002 and receives a tool, such as a tap, drill bit, driver, socket, or other tool. The mode selector 1018 is arranged to control the driving direction of the driver 1002. In some examples, the available modes include a forward mode, a reverse mode, an oscillating mode, a lock or non-rotation mode, among other modes. By switching the mode selector 1018, a user can control the rotational driving direction of the collet 1016. In the example shown, the mode selector 1018 is a collar disposed about a portion of the barrel 1008. In other embodiments, the mode selector 1018 is a button, a toggle lever, a rocker switch, or other input device.

The driver 1002 contains a motor for driving the tools at the working end. In some examples, the motor is a brushless DC motor configured to be powered from the control console 1002. In these examples, the electrical port 1010 connects the driver 1002 with the control console 1004 through the cable 1014. In other examples, the driver and console communicate wirelessly. In one example, the handle 1006 of the driver 1002 contains a motor disposed so that the motor shaft extends upwardly from the handle 1006 into the barrel 1008. A gear mechanism connects the motor shaft to a substantially horizontally extending driving shaft connected to the collet 1016 and that is utilized to drive a drilling tool or mechanized end received by the driver 1002.

Figure 14:
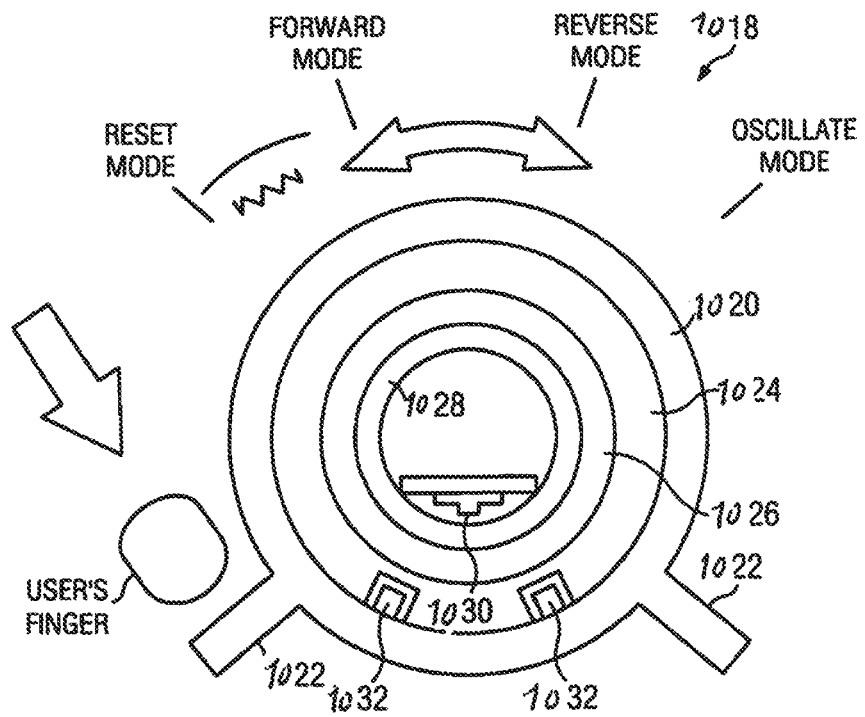
FIG. 14 is an illustration of a highly simplified cross-sectional view of a mode selector on the exemplary driver of FIG. 13.

One example of the mode selector 1018 is shown in greater detail in FIG. 14. Here, the mode selector 1018 includes a collar 1020 that includes radially projecting tabs 1022 that enable a user to easily rotate the mode selector about a central axis to change driving modes. A magnet ring 1024 is fixed to and rotates with the collar 1020. The magnet ring 1024 and collar 1020 are disposed on a portion of the body 1026 of the driver barrel 1008, with an insulating layer 1028 and Hall effect sensor 1030 disposed therein. The magnet ring 1024 includes a plurality of magnets 1032. Rotation of the mode selector 1018 displaces the magnets 1032 relative to the Hall effect sensor 1030. The Hall effect sensor 1030 generates a signal used to identify the position of the mode selector 1018, and likewise, to identify the selected mode. In the embodiment shown, the mode selector 1018 may communicate a signal representing the mode or the position of the collar to the control console 1004. Other examples of mode selectors include a single magnet 1032 and multiple hall effect sensors 1030. Other types of sensors are contemplated as being used in place of the Hall effect sensors including, for example, reed sensors and others.

The mode selector enables a user to select the operating mode of the driver 1002. In the example shown, the available modes include a forward mode, a reverse mode, an oscillating mode, and a lock or non-rotation mode, among other modes. Some designs provide ancillary user inputs not related to shaft control. The location of the magnets relative to the Hall effect sensors provides an indication of the selected mode. This is communicated back to the console 1004 for processing and functional implementation.

Returning to FIG. 13, the control console 1004 may include controls and settings for operating the driver 1002. In one example, the control console 1004 is configured to receive signals from the driver 1002 and control the output of the driver 1002 based on those received signals, combined with user settings received directly at the control console. Some examples of this may become apparent from the description below. It is worth noting that some systems do not include a separate control console, and in such embodiments, all determinations and calculations may be performed elsewhere, such as for example, onboard the driver 1002 itself.

Figure 15:
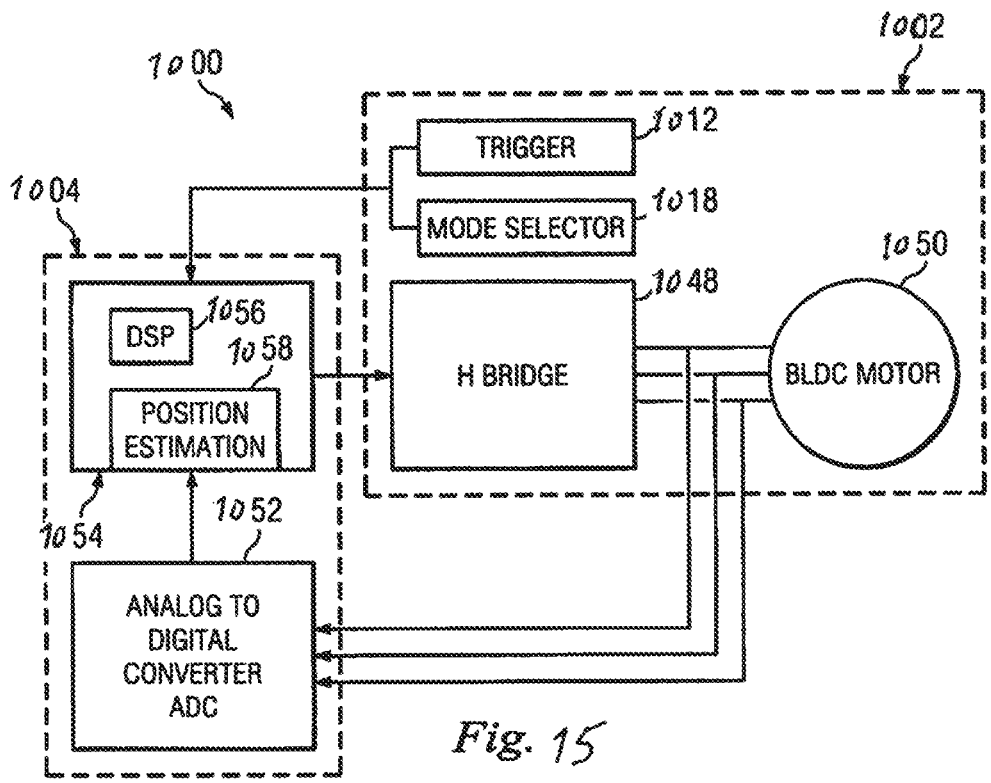
FIG. 15 is a block diagram showing functional components of the motor powered screwdriver system with an electric ratchet in accordance with one aspect of the present disclosure.

FIG. 15 shows a block diagram of one example of a system 1000 in accordance with an exemplary aspect of the present disclosure. As can be seen, the system includes the driver 1002 and the control console 1004. In this example, the driver 1002 includes the trigger 1012, the mode selector 1018, an H-bridge 1048, and a motor 1050.

The H-bridge 1048 directs power from the control console 1004 to the motor 1050. Depending on the operating mode determined by the mode selector 1018, the H-bridge directs power in one direction or the other. For example, if the mode selector 1018 is changed from forward mode to reverse mode, the H-bridge redirects power through the motor and switches its operating direction.

Figure 16:
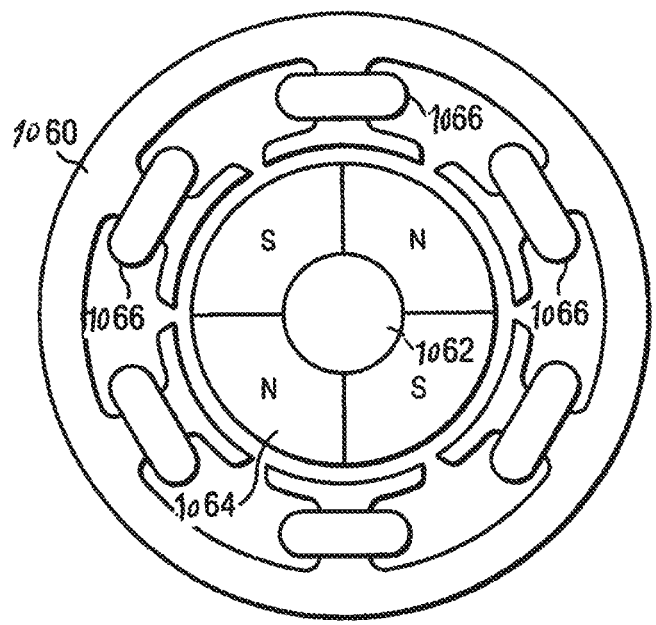
FIG. 16 is a stylized illustration of a cross-sectional view of an electric motor in accordance with an exemplary aspect of the present disclosure.

In this example, the motor 1050 is a brushless DC motor having three windings represented by the three inputs from the H-bridge 1048. FIG. 16 shows a stylized example of a brushless DC motor in accordance with one aspect of the present disclosure. The motor 1050 in FIG. 16 is a synchronous motor and includes a stator 1060, a rotor 1062, and permanent magnets 1064 disposed on and rotatable with the rotor 1062. In this example, the motor is a 3-phase motor, although 2-phase and single phase motors may be used in other embodiments. The stator 1060 includes windings 1066. In this example, the magnets 1064 include two pole pairs with alternate north and south poles. Thus, the example shown is a four pole motor. However, in another example, only a single pole pair motor, or two pole motor, is used. Other embodiments include substantially more pole pairs. Some examples have up to eight pole pairs or more, with the more pole pairs being present, the more exact control can be determined. As in conventional motor systems, the rotor 1062 rotates relative the stator 1060. The stator is fixed relative to the driver housing 1005. Accordingly, when a user physically turns the driver to effect a manual driving of a screw, the stator 1060 stays fixed relative to the driver housing 1005. In some examples, the motor has a motor housing about the stator 1060 fixed in place relative to the driver housing 1005.

Returning to FIG. 15, the control console 1004 includes a processing system and memory programmed such that the control console 1004 is configured to receive various setting inputs from a user (e.g., maximum speed and maximum torque) and to control the motor of the driver 1002 based on the user's setting inputs and depression of the trigger 1012 on the driver 1002. In that regard, the control console 1004 of the system 1000 provides position control and torque control to the motor of the driver 1002.

In this example, the control console 1004 includes an analog to digital converter (ADC) 152 and a controller 1054 that comprises a processor 1056 running a position estimation module 1058. The system 1000 also includes memory containing executable programs that influence the manner in which the system 1000 operates, a user interface, communication modules, and other standard equipment. In some examples using the control console 1004, a user is able to set the maximum speed, acceleration, jerk, and mode (forward, reverse, or oscillate) for the system. Further, the processor 1056 receives a signal indicative of the amount of depression of the trigger 1012. The signal sent to the processor 1056 may be indicative of the amount of trigger depression based on the magnetic field sensed by the Hall effect sensor, as indicated above. Also, as indicated above, all signal communication between the driver and the console may be over the cable 1014. Alternatively, communication may be wireless Bluetooth, Wi-Fi, conventional RF, infrared, or other communication method.

In the example shown, the processor 1056 is a digital signal processor that receives the various setting inputs from the user. Based on the settings, and particular pre stored executable programs, the processor controls the H-bridge and sends signals to the H-bridge, which are communicated to the motor 1050. For example, using the inputs received with respect to the maximum speed, acceleration, jerk, mode, and trigger position, the position of the rotor of the driver 1002. The controller 1054 outputs a pulse-width modulated control signal that has a duty cycle in accordance with a desired control curve to control the position of the rotor of the motor.

In this example, the control console 1004 uses the back electromotive force (EMF) from the motor 1050 to monitor the rotor position of the motor 1050 to ensure that the motor's rotor is achieving the desired positions defined by the control curve. This is accomplished by detecting the EMF level for each winding in its turn at the controller 1054. The EMF signals are sent from the motor to the ADC, which converts the EMF signals to digital signals, which are then communicated to the controller 1054. During standard operation, if the rotor is not achieving the desired positions (e.g., the rotor has rotated too far or not far enough) as detected by the EMF, then the controller 1054 adjusts the duty cycle based on an error signal representative of the difference between the actual position of the rotor and the desired position of the rotor. In this manner, the system 1000 monitors the position of the rotor to ensure that the rotor is achieving the desired positions during use of the driver 1002.

In the driver 1002, the stator 1060 (FIG. 16) is fixed in place relative to the driver housing 1005 (FIG. 13). The motor rotor 1062 is at least rotatably, mechanically coupled to the drive shaft and collet 1016 either directly or through a gear system, for example. Therefore, movement of the rotor 1062 relative to the stator 1060 is indicative of movement of the collet 1016 (and a tool in the collet) relative to the driver housing 1005. Accordingly, when the collet 1016 and the drive shaft are engaged with a tool, which may be engaged to a screw, the system 1000 can detect relative movement between the screw and the driver 1002. In this example, the controller 1054 of the system 1000 is configured to operate the electric ratchet by receiving data, such as EMF indicative of the rotor position relative to the stator and applying power to the motor at a level sufficient to reduce or prevent further detected relative movement between the rotor and the stator.

Figure 17:
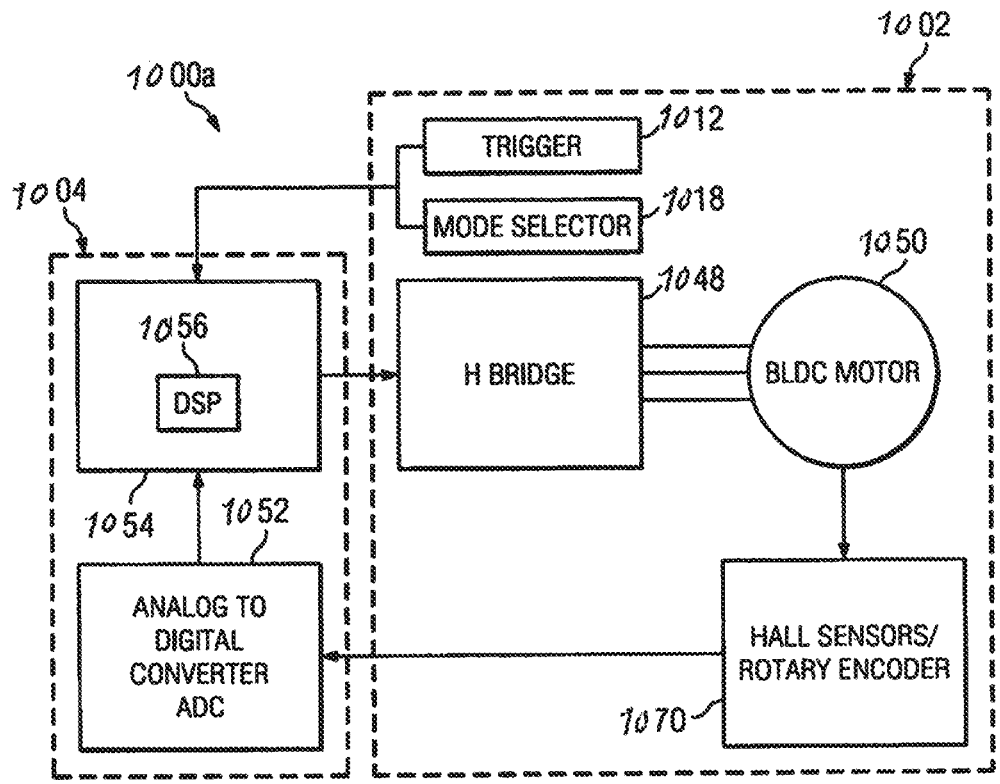
FIG. 17 is a block diagram showing functional components of the motor powered screwdriver system with an electric ratchet in accordance with one aspect of the present disclosure.

FIG. 17 shows a block diagram of an example of a system 1000a in accordance with another exemplary aspect of the present disclosure. As can be seen, the system 1000a includes the driver 1002 and the control console 1004. In this example, the driver 1002 includes the trigger 1012, the mode selector 1018, the H-bridge 1048, and the motor 1050. However, this embodiment also includes a position sensing element 1070. The position sensing element 1070 configured to directly identify the position of the rotor in the motor 1050. In one example, the position sensing element 1070 is a plurality of Hall effect sensors. In this example, the Hall effect sensors are disposed in the stator of the motor and are configured to detect the passage of the magnetic poles of the rotor and emit a voltage signal that is passed to the control console 1004. One example uses three Hall effect sensors. However, greater and smaller numbers of Hall effect sensors are contemplated.

In FIG. 17, the control console 1004 includes the ADC 1052 and the controller 1054. However, here, the controller 1054 can receive data directly indicating the position of the rotor, and therefore, the controller need not include a position estimation module 1058. As described above with reference to FIG. 15, the ADC 1052 converts the voltage signal from the position sensing element 1070 to a digital signal and passes it to the controller 1054. In this example, instead of determining position as required by the system 1000 in FIG. 15, the controller 1054 directly detects the position of the rotor relative to the stator. The controller 1054 may then operate the motor 1050 based on the position of the rotor to prevent or limit freewheel rotation in one direction while permitting freewheel rotation in the other direction, thereby achieving the ratcheting effect. Although described as Hall effect sensors, the position sensing element 1070 may also be a rotary encoder or other direct position measuring system that will measure the position of the rotor 1062 relative to the stator 1060.

Figure 18:
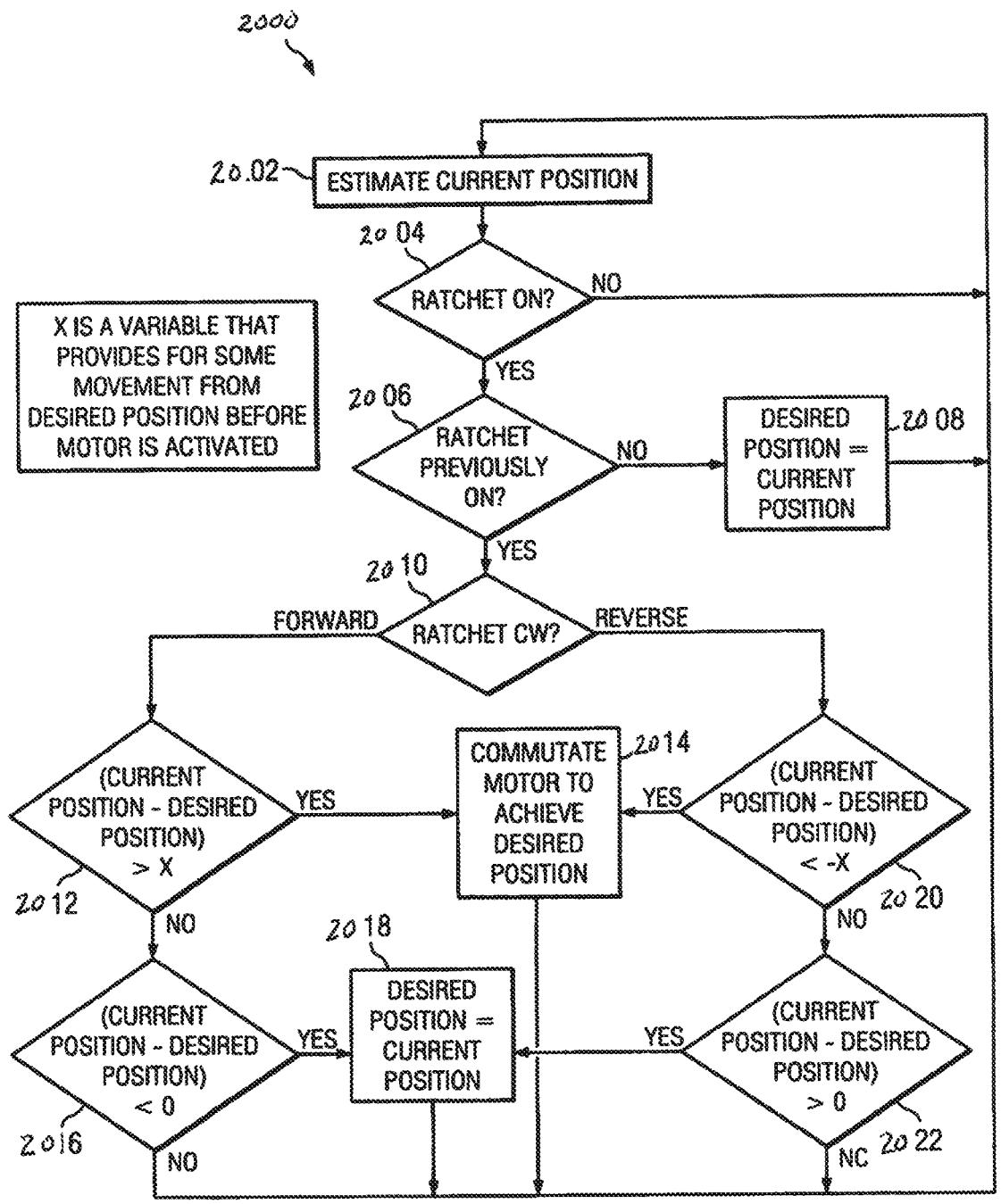
FIG. 18 is a flow chart showing control logic in accordance with one exemplary aspect of the present disclosure.

This is explained further with reference to FIG. 18, which shows a logic flow chart performed by the controller 1054 to achieve the electric ratchet functionality of the powered screwdriver system 1000. In one example the logic flow chart is an executable program of a method stored in memory and executable by the processor 1056. The method, referenced by the numeral 2000, begins at a step 2002 where the processor 1056 estimates the current position of the rotor relative to the stator. This may be accomplished in any of a number of methods, including those methods described above where the controller 1054 monitors EMF from the motor 1050, and based on the EMF determines the position of the rotor or where the controller 1054 receives signals from Hall effect sensors or encoders associated with the motor that indicate the position of the rotor relative to the stator.

At a step 2004, the controller determines whether the ratchet mode is on or active. In one example, this is accomplished by detecting the position of the mode selector 1018. If the mode selector 1018 is at a position where the ratcheting mode is active, then a signal is sent from the driver 1002 to the control console 1004 for processing by the controller 1054. The signal permits the controller to operate the system 1000 in a ratcheting mode. In some examples, the signal is the absence of alternative signals. In the mode selector 1018 described above, the ratcheting mode is active in a forward direction anytime the mode selector 1018 is in a forward mode and the trigger is not depressed. The ratcheting mode is active in a reverse direction anytime the mode selector 1018 is in a reverse mode and the trigger is not depressed. In other examples, the mode selector includes a ratcheting mode independent of the forward and reverse modes. Accordingly, a user may activate or turn on the ratchet mode by moving the mode selector to a ratchet mode. Mode selectors may include buttons or switches independent of the mode selector described above, and may be disposed on the console 1004 or on the driver 1002. If, at step 2004, the ratchet mode is not on, then the system cycles in a loop, continuing to estimate the current position of the rotor relative to the current position. In this condition, the driver may still operate in normal functions, permitting forward driving, reverse driving, or oscillating, among other control scenarios.

If at step 2004, the ratchet mode is on, then the controller 1054 determines whether the ratchet was previously on or whether this is the first time through the loop at a step 2006. If it is the first time through the loop at step 2006, then the loop sets a desired position of the rotor relative the stator. Here, it sets the desired position as equal to the current position at a step 2008. The step of setting the desired position equal to the current position at step 2008 uses the current position that was estimated at step 2002. With the desired position set at step 2008, the process returns to step 2002 and again estimates the current position of the rotor relative to the stator. This estimated current position value is stored for later use.

If the ratcheting mode was previously active or on at step 2006, then the controller 1054 determines whether the ratchet is set for forward (clockwise) or reverse (counterclockwise) rotation at step 2010. In some embodiments, the direction of rotation is associated entirely with the setting of the mode selector. For example, if the mode selector is set in a forward mode, then the direction may be set as forward. If the mode selector is set in a reverse mode, then the direction selector may be not set as forward, but instead is set at reverse. In some examples, as indicated above, the system 1000 may be configured to ratchet in only a single direction. Accordingly, the direction selector at step 2010 may also be a condition for determining whether the ratchet is on and therefore, in some examples may be a part of step 2004.

In this example, where the ratcheting may be selected to be forward or reverse, the method continues from step 2010 depending on the direction selected. If the direction is forward at step 2010, then the method determines the difference between the desired position and the current position last taken at step 2002. This difference is referred to herein as an error value. The error value is then compared to a preset threshold value x to determine whether to use the motor to counter applied loading and use the system as a ratchet. The threshold value x is a variable that provides for some movement from the desired position before the motor is activated. In some examples however, the value x is zero or substantially zero.

At step 2012, if the error value between the current and the desired positions is greater than the preset value x, then the controller 1054 commutates the motor to achieve the desired position at a step 2014. Accordingly, as the driver housing begins to displace relative to the collet and driving tool in the driver 1002, the error value between the current position and the desired position increases until it exceeds the preset value x. Once the error value is greater than x, the controller 1054 controls the motor with power sufficient to effectively offset the torque being applied to maintain the rotor substantially in the desired position relative to the stator. This need not necessarily require bringing the error to zero, but may be include merely limiting or controlling further increases in the error value. Thus, as a user rotates the driver 1002 forward without depressing the trigger 1022, the motor substantially maintains the rotor position relative to the stator, thereby manually driving the hardware, such as a bone screw. Further, since the threshold value of x may be in micro degrees, the relative displacement may be imperceptible to a user. In one example, the value of x amounts to less than one degree of relative movement.

If at step 2012, the error value between the current and desired positions is less than the value of x, then the processor 1054 determines at a step 2016 whether the error value is less than zero. A value less than zero at step 2016 indicates that the rotor 1062 is being turned in reverse relative to the stator 1060. Consistent with conventional mechanical ratchet operation, freewheel rotation in one direction is permitted while rotation in the other direction is not. Accordingly, in this embodiment, the motor is not controlled to limit or prevent rotation in the reverse direction at step 2016. Accordingly, if the error value between the current and desired positions is less than zero, then the controller 2054 resets the desired position to the detected current position at step 2018. This provides a new starting point (desired position).

If at step 2016, the error value between the current and desired position is not less than zero, but was also not greater than x at step 2012, then the controller returns to step 2002 and begins the process again.

Returning now to step 2010, if the ratchet setting were not set for forward ratcheting, then in one example, the controller 1054 determines the error value between the current position and the desired position and compares it to a negative value of x (−x) at step 2020. Operation then operates in a manner similar to that described above with reference to steps 2012, 2014, 2016, and 2018, but using the opposite direction, resulting in a negative x. That is, if the error value is less than negative x, then the controller 1054 controls the motor to maintain the current position at the desired position at step 2014. As such, the system effectively limits or prevents relative movement of the driver 1002 and the collet or a screwdriver in the collet. If the error value between the current and desired positions is not less than negative x, then the controller 1054 determines whether the error value is greater than zero at a step 2022. If the error value is greater than zero, then at step 2018, the desired position it set equal to the current position. If is not greater than zero, then the processor returns to step 2002.

The method 2000 described in FIG. 16 is for a system that permits ratcheting in both the forward and rearward directions, depending on the setting. Some embodiments permit ratcheting in only one direction, such as a forward driving direction. In such a system, the steps 2020 and 2022 may not be present. Because the motor is powered to prevent or limit relative movement between the collet and the driver 1002, a user can drive the instrument or tool, whether a screw, a tap, a bit or other instrument or tool, by rotating the driver 1002 in a forward direction without depressing the trigger.

In one example, the system 1000 is configured so that when the driver is manually rotated in the freewheeled rotation direction, the driver 1002 or control console 1004 emits a clicking sound. For example, the clicking sound may be emitted when the system is in a ratchet mode and the collet displaces relative to the driver body by a preset range of rotation, as measured by the displacement of the rotor relative to the stator. In one embodiment, the controller 1054 is configured to generate a signal that results in a clicking noise one time for every ten degrees of freewheeled rotation. The speaker emitting the clicking noise may be disposed on the driver 1002 or on the control console 104. Accordingly, users may hear an electronically generated clicking in the same way users may hear a mechanical generated clicking noise in a conventional mechanical system, such as toothed sprocket with pawl systems. In some examples, instead of an audible clicking noise, the PWM of the motor voltage provides audible feedback to the user. For example, as applied shaft torque increases, an audible tone generated by the motor may provide feedback to the user. In some examples, as the torque increases, the volume of the audible tone increases, or alternatively, as the torque increases, the pitch (based on frequencies) increases.

Although shown and described as having both driver and a control console, some embodiments of the present disclosure include a driver containing the processing capability that is disclosed herein as being on the control console 1004. Accordingly, in some examples, the controller 1054 is disposed on the driver itself. Further, although the embodiment shown discloses operating power being drawn from the control console 1004, some driver embodiments include their own separate power source, such as a battery power source, using either a rechargeable battery pack or primary batteries. Some embodiments include a power cord pluggable into a conventional power outlet.

In some examples the driver is a surgical tool configured to be used in a surgical setting. Accordingly, the driver may be configured in a manner to be sterilized by an autoclave. Further, the driver may be configured to be entirely self-contained, without vents or releases of material or filaments from the motor that could introduce contamination to a sterile field.

As described above, the freewheel capability of the electric ratchet includes not powering the motor to prevent motor displacement in the second freewheel direction opposite the first, driving direction. Accordingly, a user can freely rotate the driver relative to the screw in the second, opposite direction. In some embodiments, the freewheel capability of the electric ratchet also provides some small level of motor power to offset drive train drag when the motor is rotated in the second freewheel direction. Accordingly, in some examples, where the drive train drag exceeds the frictional force on the surgical hardware (such as a bone screw), the hardware still will not rotate with the driver in both the first driving and second freewheeling directions. Instead, it will rotate with the driver in the first driving direction, but the motor will operate to offset the inherent drag in the driver so that the driver does not rotate with the driver in the second freewheel direction. This provides the user with the perception that the electric ratcheting function is freewheel rotating in the second freewheel direction, although the drag forces are being overcome by the motor.

Although the present disclosure has been described with reference to preferred embodiments, workers skilled in the art will recognize that changes can be made in form and detail without departing from the spirit and scope of the present disclosure.

What is claimed is:

1. A surgical system comprising:
   a surgical handpiece comprising an electrical motor receiving a motor current and an electrically conductive driveshaft electrically insulated from the motor, the driveshaft extending along an axis and rotatable about the axis by the motor;
   a surgical tool connected to the surgical handpiece, the surgical tool electrically coupled to and rotatable by the driveshaft;
   a controller connected to the surgical handpiece and programmed to interface with the surgical handpiece, the controller including a data entry device and a display screen, wherein the controller is programmed to determine a temperature based on the motor current and to display a real-time torque value applied by the surgical handpiece on the display screen where the displayed torque value is based on the motor current, and to react to torque rate of change over time via controlling the motor current;
   a stimulator assembly electrically coupled to the driveshaft adapted to provide an electrical current stimulation directly to the driveshaft to provide nerve integrity monitoring; and
   an electric ratchet operatively associated with the driveshaft.

2. The surgical system of claim 1, wherein the controller is configured to limit a torque rate of change over time applied by the surgical handpiece based upon the motor current feedback.

3. The surgical system of claim 2, wherein the controller is configured to monitor the torque rate of change over time and detect a failure of the surgical tool or of a bone to which the surgical tool is being applied; and
   wherein the controller is programmed to stop the motor or control a current delivered to the motor if a failure is detected.

4. The surgical system of claim 1, further comprising a contact sub-assembly configured to transmit a stimulation energy to the driveshaft to provide nerve integrity monitoring.

5. The surgical system of claim 4, wherein the driveshaft comprises a first stationary state and a second rotating state and wherein the surgical handpiece is configured to provide stimulation energy to the surgical tool when the driveshaft is in one of the first state and second state.

6. A surgical system for use in spine surgery, comprising:
   a surgical handpiece comprising a motor and an electrically conductive driveshaft, the driveshaft extending along an axis and rotatable about the axis by the motor, the driveshaft coupled to the motor;
   a controller connected to the surgical handpiece and configured to monitor a torque rate of change over time to detect a failure of a surgical tool associated with the handpiece or of a bone to which the surgical tool is being applied and in response, is programmed to stop the motor or control a current delivered to the motor if a failure is detected;
   a stimulator assembly electrically coupled to the rotatable driveshaft adapted to provide an electrical current stimulation directly to the driveshaft to provide nerve integrity monitoring;
   a navigation adapter of an image guidance system coupled to the surgical handpiece via an interference fit; and
   an electric ratchet operatively associated with the driveshaft.

7. The surgical system of claim 6, wherein the drive shaft is electrically isolated from the motor via insulated components mechanically coupling the driveshaft to the motor.

8. A surgical system comprising:
- a surgical handpiece comprising a housing;
- an electrical motor disposed within the housing;
- an electrically conductive driveshaft electrically insulated from the motor, the driveshaft extending along an axis and rotatable about the axis by the motor;
- a surgical tool connected to the surgical handpiece, the surgical tool electrically coupled to and rotatable by the driveshaft; and
- a stimulator assembly electrically coupled to the rotatable conductive driveshaft to provide an electrical current to the surgical tool via the driveshaft, the stimulator assembly including an interface pin mounted to housing and electrically coupled within the housing to a subassembly, the subassembly including a contact housing electrically coupled to a subassembly contact, the subassembly contact mechanically disposed over the drive shaft and electrically coupled to the drive shaft.

9. The surgical system of claim 8 wherein the subassembly contact includes a slip ring retained by the contact housing.

10. The surgical system of claim 9 wherein the contact housing provides a solder cup for connection to wiring, the wiring coupled to the interface pin.

* * * * *